(12) United States Patent  (10) Patent No.: US 8,786,849 B2
Korb et al.  (45) Date of Patent: Jul. 22, 2014

(54) METHOD FOR MEASURING AN OPTICAL SYSTEM

(71) Applicant: Carl Zeiss SMT GmbH, Oberkochen (DE)

(72) Inventors: Thomas Korb, Schwaebisch Gmuend (DE); Christian Hettich, Constance (DE); Michael Layh, Altusried (DE); Ulrich Wegmann, Koenigsbronn (DE); Karl-Heinz Schuster, Koenigsbronn (DE); Matthias Manger, Aalen-Unterkochen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 13/913,212

(22) Filed: Jun. 7, 2013

(65) Prior Publication Data

US 2013/0271749 A1  Oct. 17, 2013

Related U.S. Application Data

(63) Continuation of application No. PCT/EP2011/070755, filed on Nov. 23, 2011.

(60) Provisional application No. 61/421,317, filed on Dec. 9, 2010.

(30) Foreign Application Priority Data

Dec. 9, 2010 (DE) .......................... 10 2010 062 763

(51) Int. Cl.
*G01N 21/00* (2006.01)
*G01N 21/94* (2006.01)
*G01N 21/95* (2006.01)

(52) U.S. Cl.
CPC ............ *G01N 21/94* (2013.01); *G01N 21/9501* (2013.01)
USPC ..................................... 356/237.3; 356/237.1

(58) Field of Classification Search
CPC ........................... G01N 21/9501; G01N 21/94
USPC ............................ 356/237.1–237.5, 399–401
See application file for complete search history.

(56) References Cited

U.S. PATENT DOCUMENTS 4,357,676 A * 11/1982 Brown .......................... 708/816
6,048,651 A    4/2000 Brunner et al.

(Continued)

FOREIGN PATENT DOCUMENTS

DE        10109929 A1    11/2001
DE    102004046542 A1    3/2006

(Continued)

OTHER PUBLICATIONS

Office Action mailed on Jan. 8, 2014, directed to Taiwanese Patent Application TW 100145001 with English translation, 7 pages.

*Primary Examiner* — Michael P Stafira
(74) *Attorney, Agent, or Firm* — Edell, Shapiro & Finnan LLC

(57) ABSTRACT

First test beams (464*a-d*), after passing through an optical system on optical paths that differ in pairs, impinge on a first measurement region (461) at angles that differ in pairs with respect to the measurement plane. Second test beams (465*a-d*), after passing through the optical system on optical paths that differ in pairs, impinge on a second measurement region (462) at angles that differ in pairs, wherein the second region differs from the first. A value of a first measurement variable of the test beam at the first region is detected for each of the first test beams, and comparably for a second measurement variable at the second region for the second test beams. Impingement regions (467*a-d*) on reference surface(s) (466, 471) of the optical system are determined and a spatial diagnosis distribution of a property of the reference surface(s) for each test beam is calculated.

31 Claims, 26 Drawing Sheets

(56) References Cited

U.S. PATENT DOCUMENTS

| | | | |
|---|---|---|---|
| 6,151,101 A * | 11/2000 | Okino | 355/53 |
| 2002/0145717 A1* | 10/2002 | Baselmans et al. | 355/55 |
| 2006/0118703 A1 | 6/2006 | Wegmann et al. | |
| 2008/0144043 A1 | 6/2008 | Wegmann et al. | |
| 2009/0079952 A1 | 3/2009 | Mann | |
| 2010/0034349 A1 | 2/2010 | Kraus et al. | |
| 2011/0134408 A1 | 6/2011 | Kuramoto | |

FOREIGN PATENT DOCUMENTS

| | | |
|---|---|---|
| DE | 102007055096 A1 | 5/2008 |
| DE | 102008000551 A1 | 10/2008 |
| TW | 200730867 A | 12/1995 |
| TW | 200912558 A | 8/1997 |
| TW | 200928602 A | 9/1997 |
| TW | 200931207 A | 7/1998 |

* cited by examiner

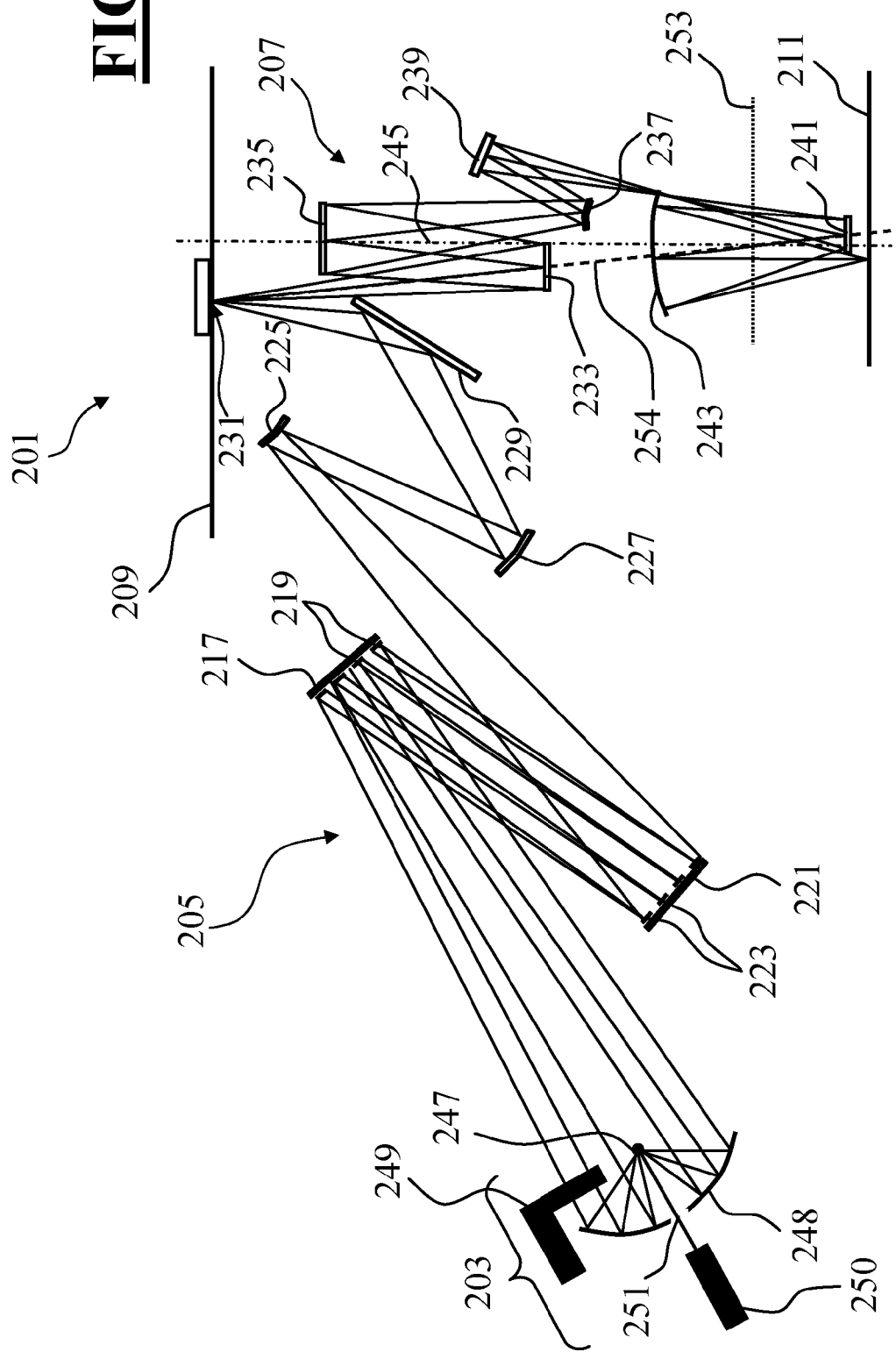

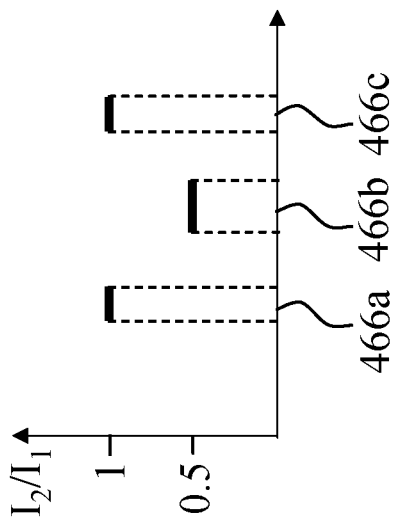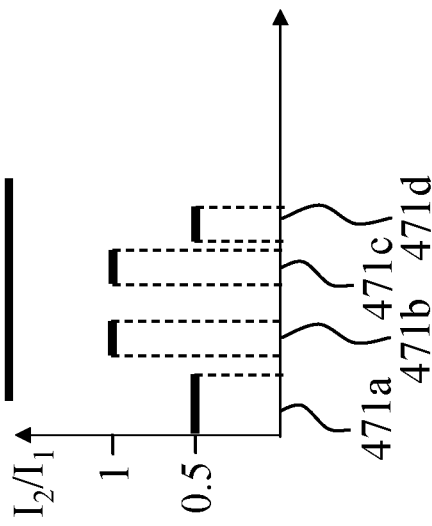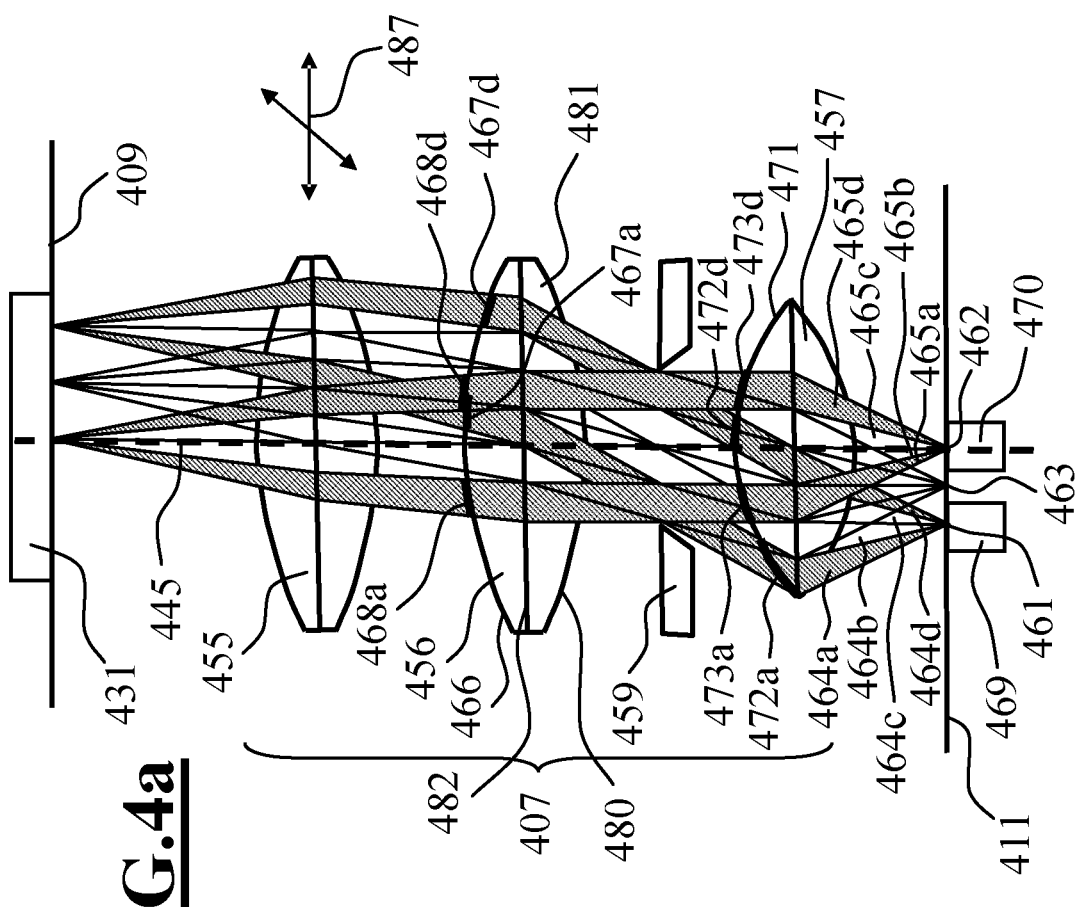

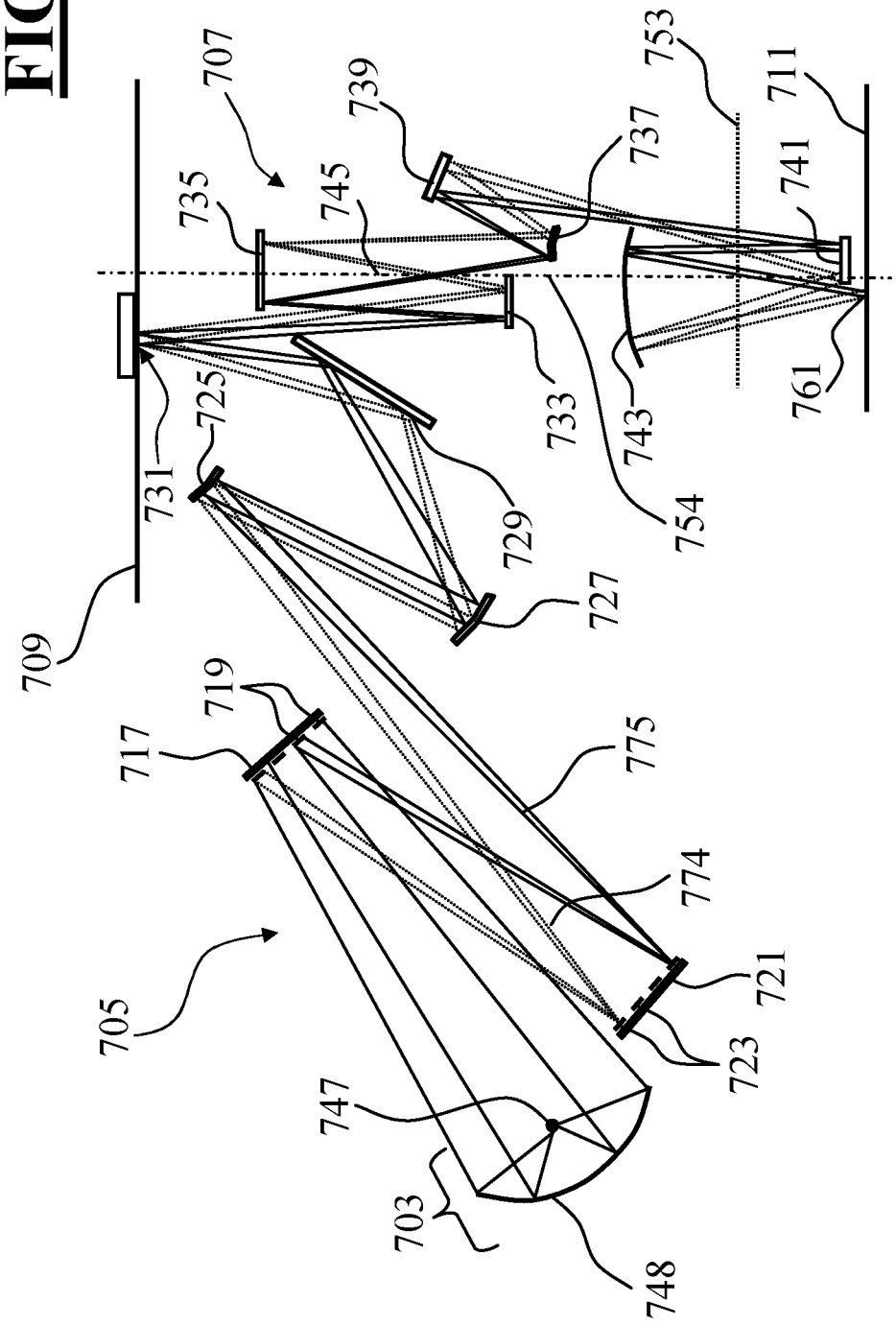

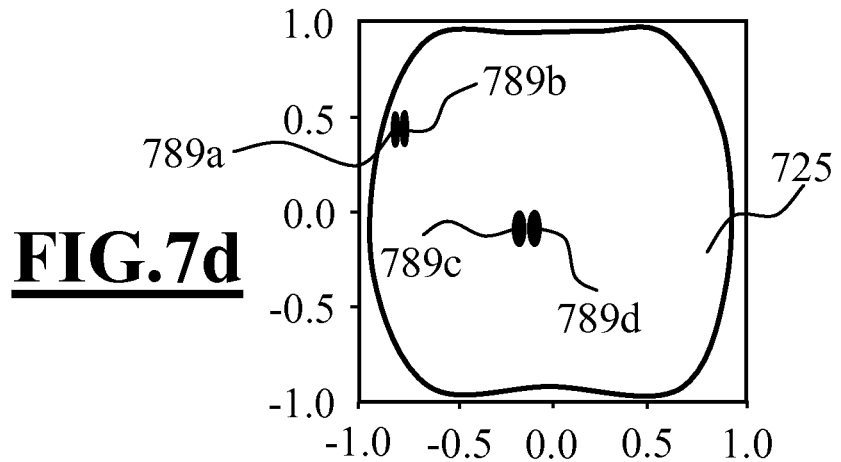
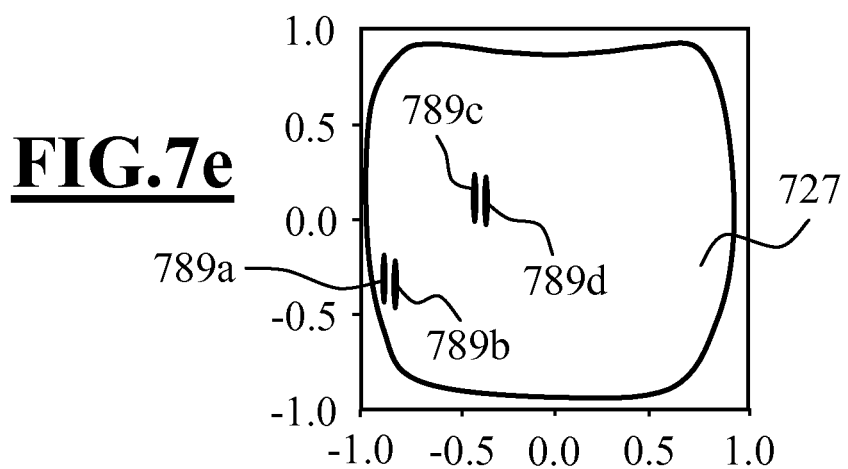
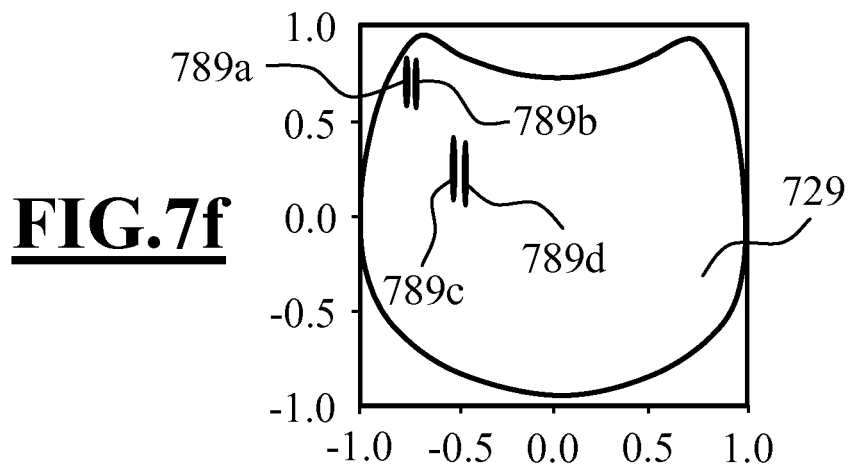

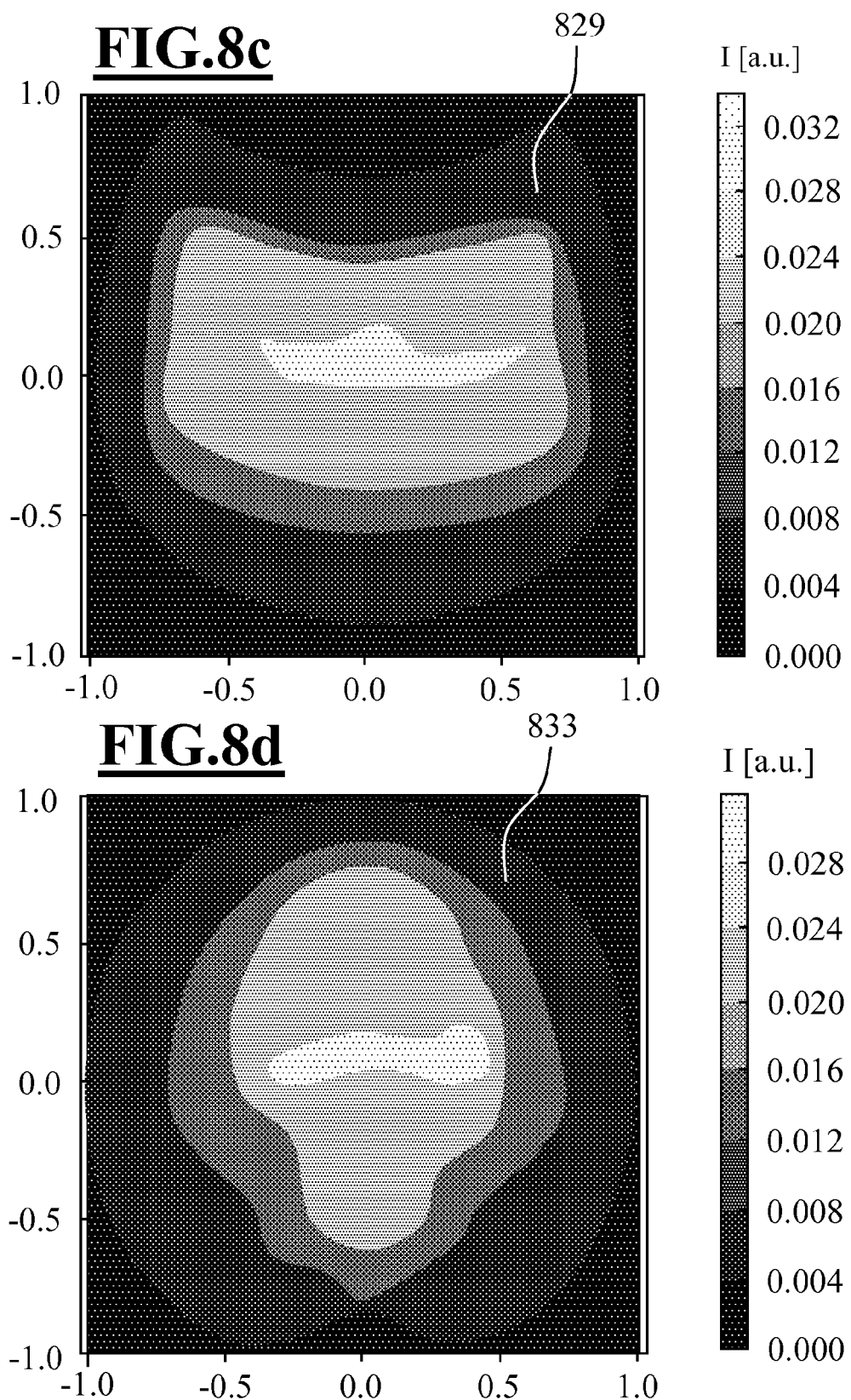

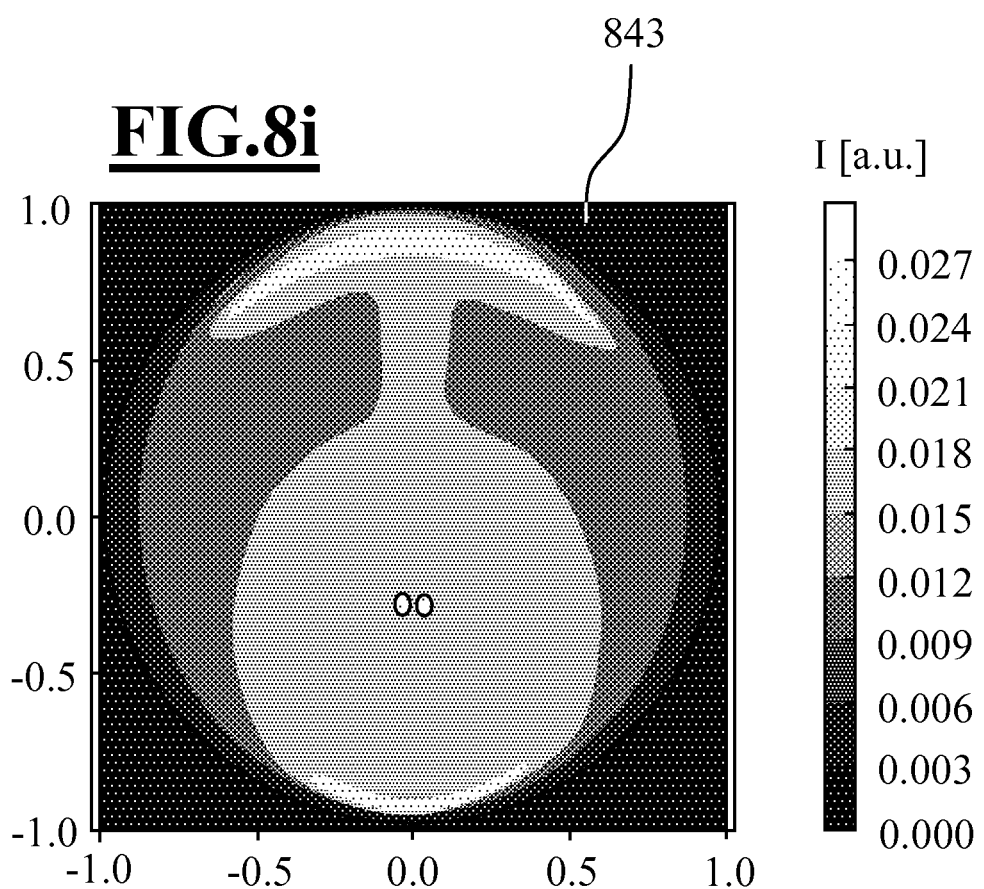

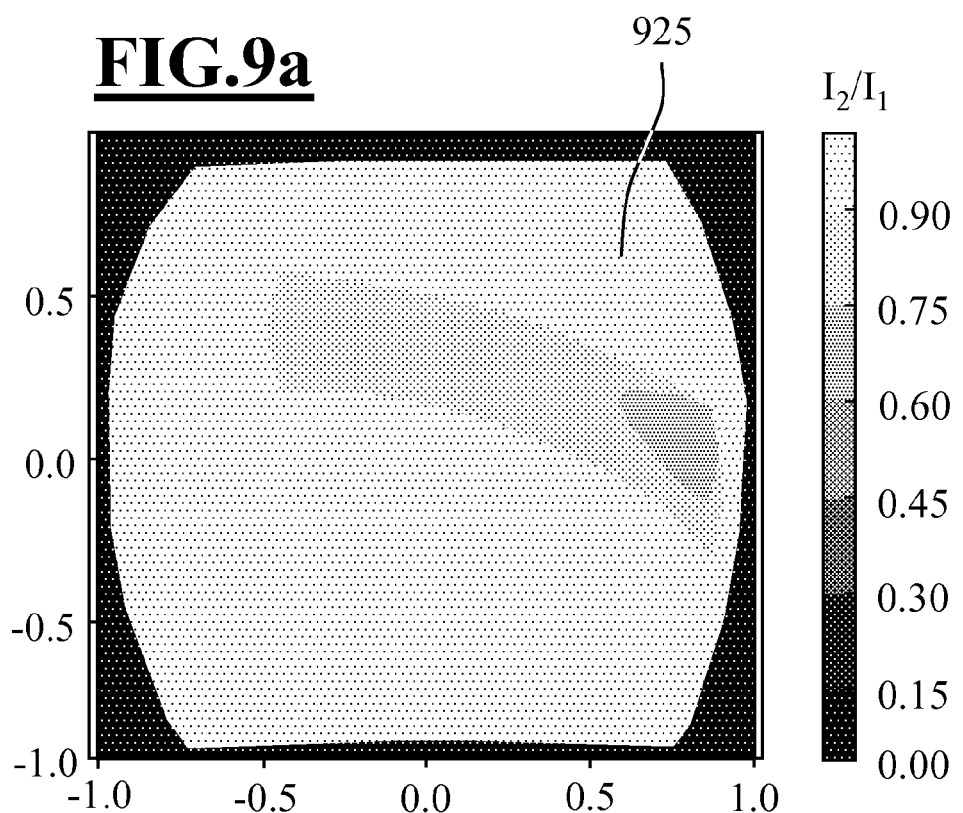
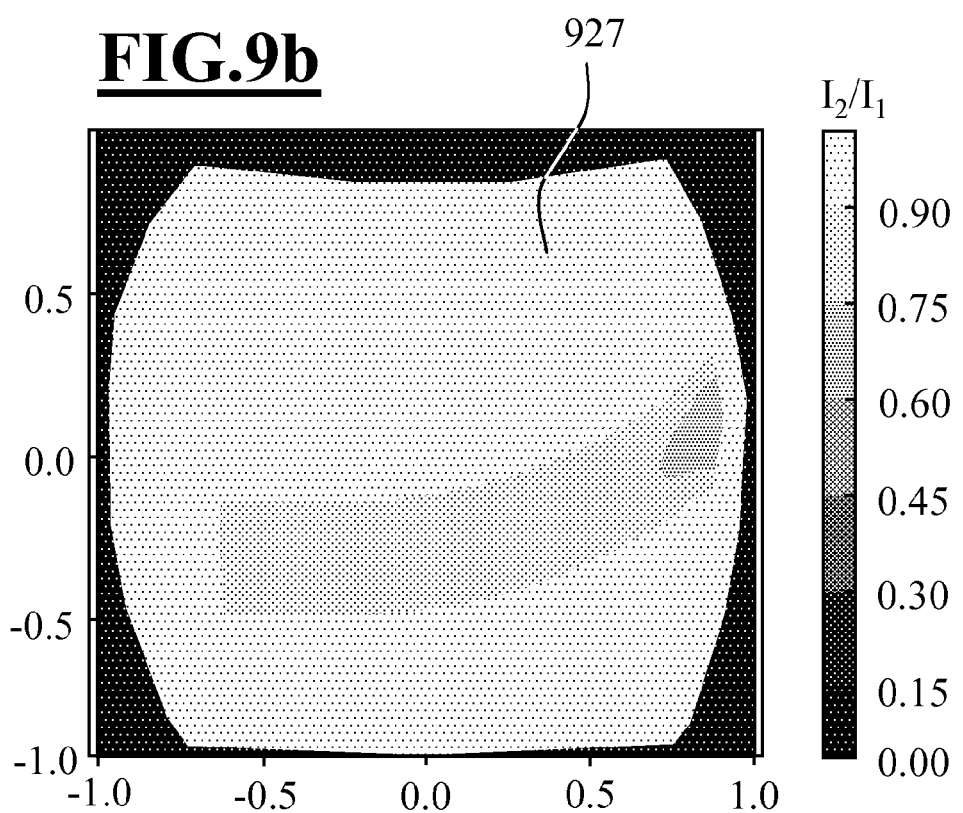

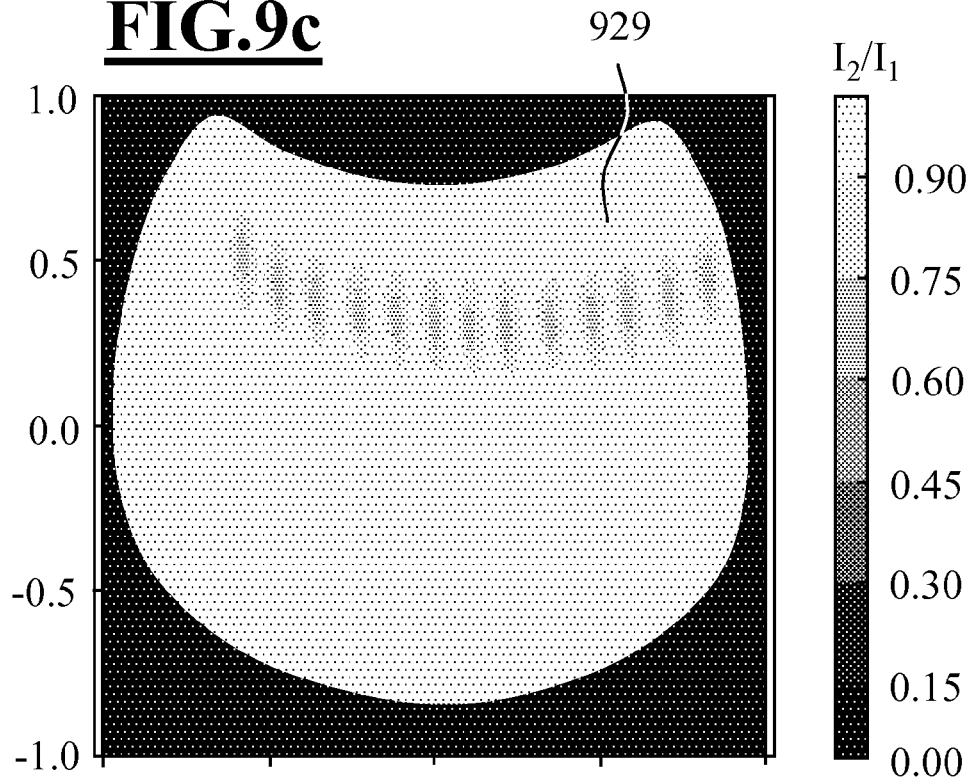
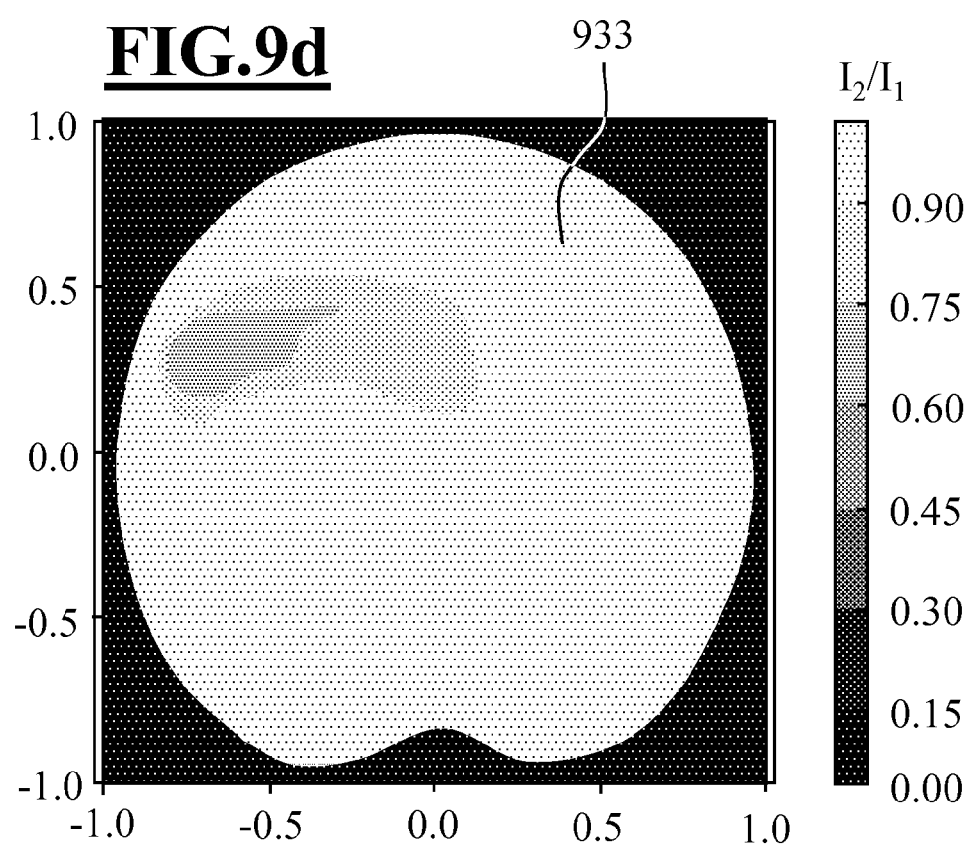

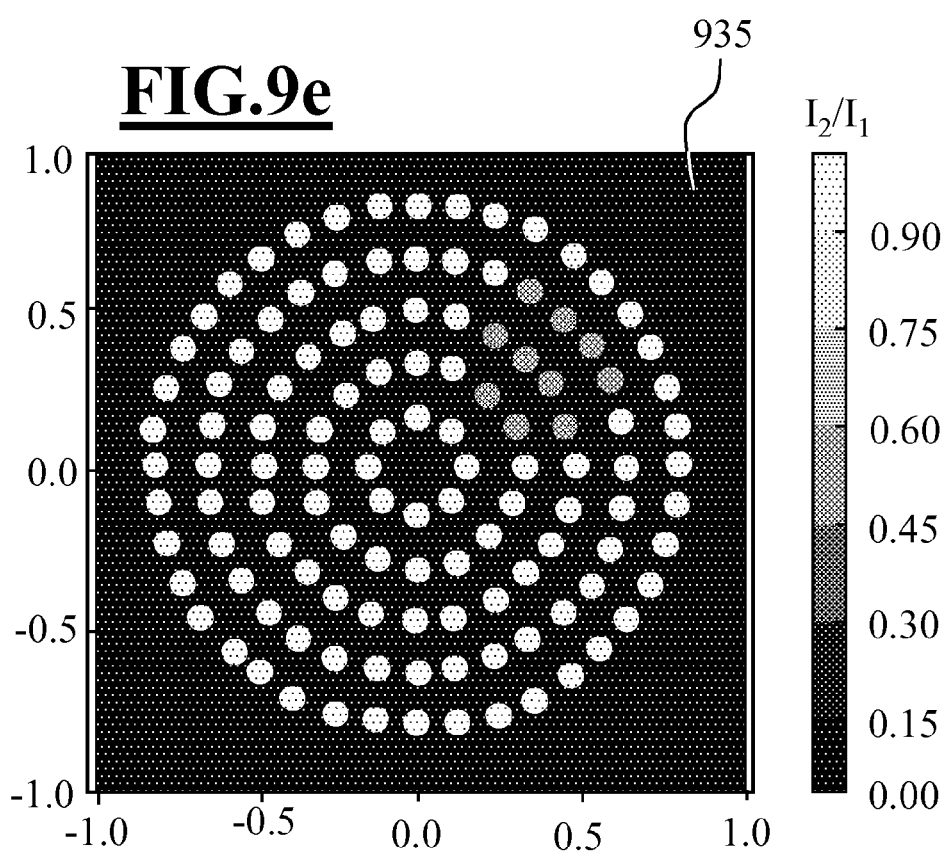
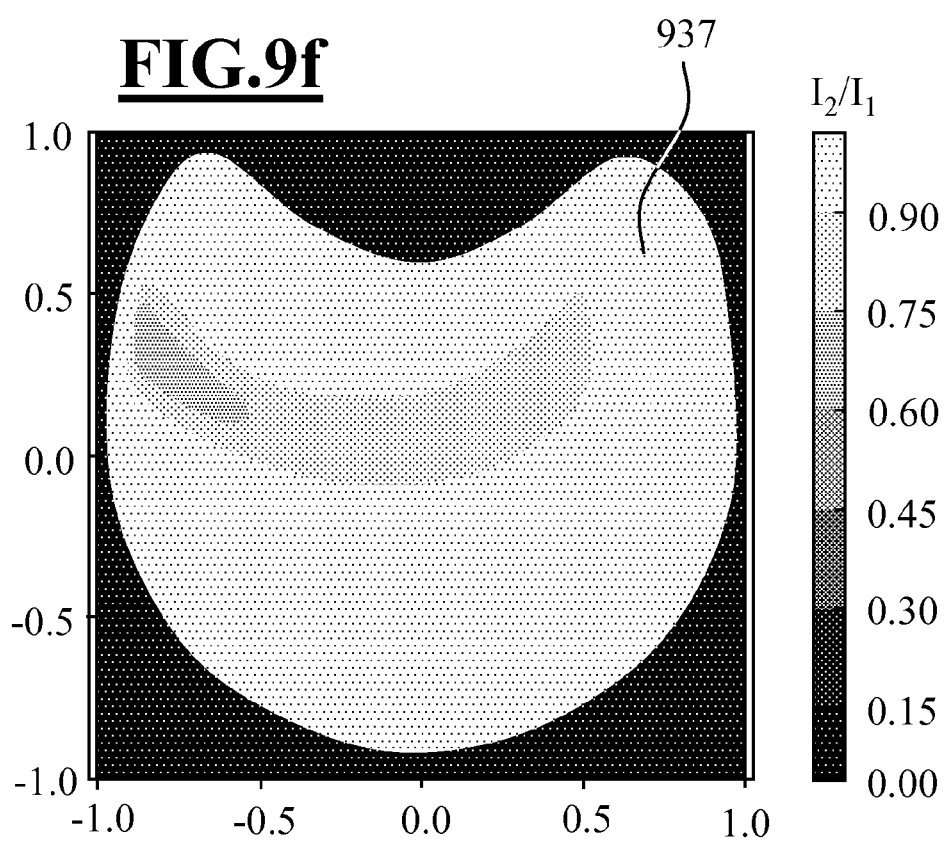

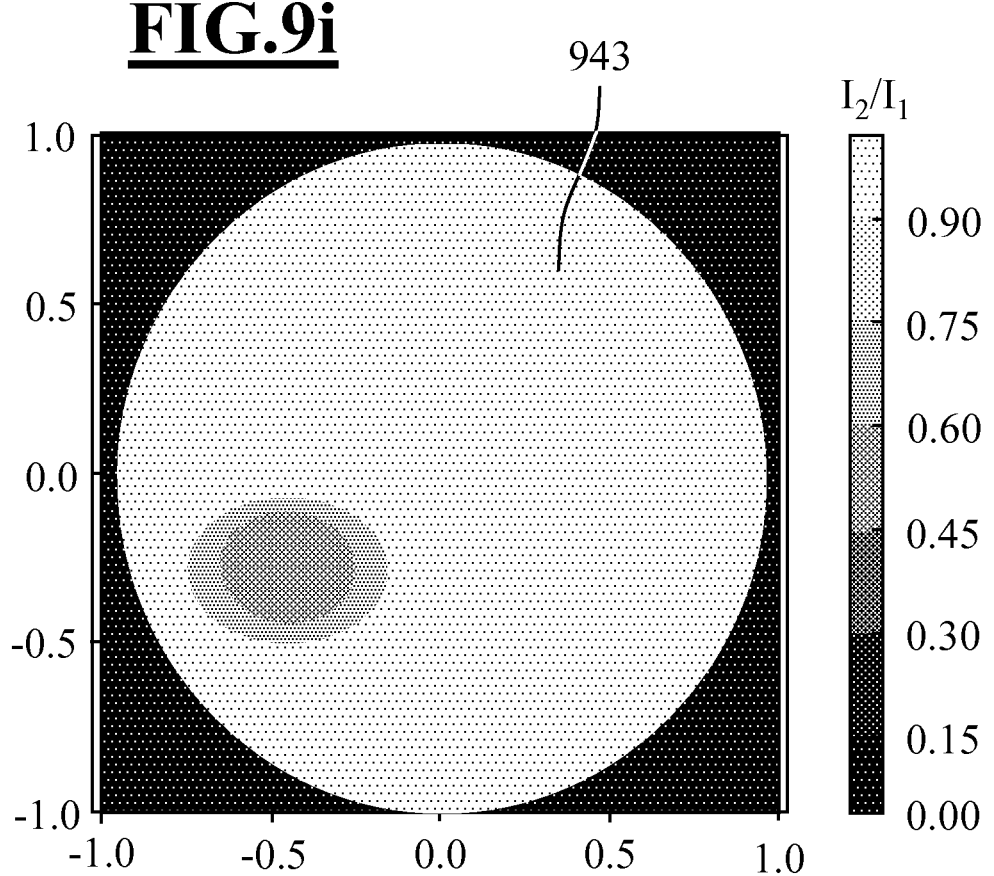

METHOD FOR MEASURING AN OPTICAL SYSTEM

The present application is a Bypass Continuation of International Application No. PCT/EP2011/070755, filed on Nov. 23, 2011, which claims priority from German Patent Application 10 2010 062 763.1, filed on Dec. 9, 2010, and also from U.S. Provisional Application No. 61/421,317, filed on Dec. 9, 2010. The contents of these prior applications are hereby incorporated by reference in their respective entireties into the present application.

FIELD OF AND BACKGROUND OF THE INVENTION

The present invention relates to a method for measuring an optical system comprising a projection lens, a computer program product for operating a measuring system for an optical system, and a microlithography projection exposure apparatus comprising a computer system comprising a computer program product of this type. Furthermore, the invention relates to a method for monitoring an optical system comprising a projection lens and a method for correcting an optical system comprising a projection lens.

Microlithography projection exposure apparatuses serve for producing microstructured components using a photolithographic method. In this case, a structure-bearing mask, the so-called reticle, is illuminated with the aid of a light source unit and an illumination optical unit and is imaged onto a photosensitive layer with the aid of a projection optical unit. For this purpose, the structure-bearing mask is arranged in an object plane of the projection lens and the photosensitive layer is arranged at the location of an image plane of the projection optical unit. In this case, the light source unit makes available a radiation which is directed into the illumination optical unit. The illumination optical unit serves for making available at the location of the structure-bearing mask a uniform illumination with a predetermined angle-dependent intensity distribution. For this purpose, various suitable optical elements are provided within the illumination optical unit. The structure-bearing mask illuminated in this way is imaged onto a photosensitive layer with the aid of the projection optical unit. In this case, the minimum feature size which can be imaged with the aid of a such a projection optical unit is influenced by various factors.

Firstly, the smaller the wavelength of the radiation used, the smaller the structures which can be imaged. For this reason, it is advantageous to use radiation having the wavelength of 5 nm to 15 nm.

Secondly, it is necessary for the optical elements of the illumination optical unit and/or projection optical unit to be manufactured and positioned highly precisely. Even a small deviation in the position or the surface form from the desired values leads to an impairment of the imaging quality.

Furthermore, impairments of the imaging quality can occur as the operating duration of the microlithography projection exposure apparatus increases. This is caused, for example, by degradation of layers on optical elements, contaminations (that is to say deposits of impurity particles) on surfaces of an optical element of the optical system, but also as a result of deformations of optical elements as a result of the long-term loading with radiation from the light source unit (compaction of lens element and/or mirror materials).

In addition, fluctuations in the quality of the radiation which is provided by the light source unit can also occur as well. Disturbances in the light source unit lead, for example, to a changed intensity distribution and/or angular distribution at the entrance of the illumination optical unit. As a result of this, the imaging mask in the image plane is not illuminated as uniformly as desired or is not illuminated with the required angular distribution, and so the imaging quality is impaired as a result of this as well.

On account of the multiplicity of optical elements from which the optical system of the microlithography projection exposure apparatus is constructed, and on account of the multiplicity of disturbances described above, it is difficult to deduce from an impairment of the imaging quality the optical element at which a disturbance is present and what disturbance has occurred.

OBJECTS AND SUMMARY OF THE INVENTION

Therefore, an object addressed by the present invention is that of providing the person skilled in the art with aids in order to be able to delimit the location and the type of the disturbance in a simple manner.

According to one formulation, this object is achieved by a method for measuring an optical system at the location of a measurement plane. The method includes:

passing a first plurality of test beams of a radiation through the optical system, so as to impinge on a first single measurement region in a measurement plane, wherein the test beams of the first plurality of test beams pass through the optical system on optical paths that differ in pairs and impinge on the first measurement region at angles of incidence that differ in pairs with respect to the measurement plane, passing a second plurality of test beams of a radiation through the optical system, so as to impinge on an identical second measurement region in the measurement plane, wherein the test beams of the second plurality of test beams pass through the optical system on optical paths that differ in pairs and impinge on the second measurement region at angles of incidence that differ in pairs with respect to the measurement plane, wherein the second measurement region differs from the first measurement region, detecting at least one associated measurement value of a first measurement variable of the test beam at the location of the first measurement region, using a measuring device, for each test beam of the first plurality of test beams, detecting at least one associated measurement value of a second measurement variable of the test beam at the location of the second measurement region, using a measuring device, for each test beam of the second plurality of test beams, determining an associated impingement region on at least one reference surface of the optical system using a database for each test beam of the first plurality of test beams and of the second plurality of test beams, wherein the impingement region associated with a test beam is defined as the surface region of the at least one reference surface on which radiation of the respective test beam impinges, and calculating a spatial diagnosis distribution of at least one property of the at least one reference surface from the measurement values and the impingement regions for each test beam.

The spatial diagnosis distribution of a property of a reference surface is understood to mean a function which allocates a numerical value to each location of the reference surface which is passed by one of the test beams. This respective numerical value describes a property of the impinging test beams at this location or the influence of the reference surface on the impinging test beams at this location.

In this case, an idealized model of the optical system is used for calculating the spatial diagnosis distribution. In this model, the properties of all the optical elements and of the light source unit are known in advance. Consequently, the influence of the optical system on the test beams is also known and the measurement values for the test beams can be predicted. If the measurement values that are measured then have a deviation from the measurement values that are expected, this means that the optical system deviates from the idealized model in an unexpected manner, in particular that one of the disturbances explained above is present in the optical system. According to the invention, the intention is now to provide for the user of the optical system an aid in order to be able to delimit the nature of the disturbance present more exactly. The idealized model system is used for this purpose. In the context of the model system, the exact profile of all the test beams is known. Therefore, for an arbitrarily chosen reference surface of the optical system, the impingement regions of all the test beams on said reference surface are also known. Furthermore, in the context of the model system, the influences of all the optical elements on the test beams are also known. The model system is then used to calculate from the measured measurement values what properties the test beams at the location of a specific reference surface would have to have in order to lead to the measured measurement values within the model system. This spatial distribution of the properties of the test beams on the reference surface thus forms a special case for a spatial diagnosis distribution.

In a further-reaching interpretation it is assumed that the reference surface is responsible for the deviation of the measurement values. A specific desired distribution of the properties of the test beams on the reference surface is expected within the model system. Since the measured measurement values then deviate from the expected measurement values, it inevitably emerges that the spatial distribution of the properties of the test beams on the reference surface also deviates from the expected desired distribution. This deviation can be caused, for example, by the reference surface having an unexpected influence on the test beams. This can be the case if unexpected damage to the reference surface is present. The model system is then used to calculate from the measured measurement values what influence the reference surface would have to have on the test beams in order to lead to the measured measurement values within the model system. Therefore, within the model system, a filter function for the reference surface is calculated, which indicates how the reference surface would have to influence the test beams such that the measured measurement values would arise. This spatial distribution, which parameterizes the influence of the reference surface on the impinging test beams at this location, is therefore likewise a special case for a spatial diagnosis distribution.

In one embodiment, by way of example, the radiation power of the radiation of the respective test beams at the location of the respective measurement regions is detected. From these measurement values, the diagnosis distribution of the radiation intensity on at least one reference surface can be determined with the aid of the method according to the invention. The diagnosis distribution of the radiation intensity of the reference surface indicates what radiation intensity is present on account of the test beams in the model system at each location of the reference surface. That is to say that indicates what radiation intensity would be present at each location of the reference surface on account of the test beams if the remaining components of the optical system had a previously defined influence on the radiation power of the test beams.

In some embodiments, this influence of the remaining components of the optical system on a test beam can be described by a correction factor. In one embodiment it is assumed, for example, that the remaining components of the optical system have no influence on the radiation power of the test beams. The correction factor for all the test beams is therefore equal to one. In another embodiment, the correction factor for each test beam corresponds to the reciprocal of an attenuation experienced by the radiation power of the associated test beam along the optical path between the at least one reference surface and the measurement plane. This has the effect that the spatial diagnosis distribution of the radiation intensity in the model system better corresponds to the physical distribution of the radiation intensity at the location of the reference surface. The better correspondence arises since the model system used comes closer to the real optical system on account of the adapted correction factors.

The spatial diagnosis distribution of the radiation intensity firstly makes it possible to monitor a light source unit with which the optical system is operated. A deviation of the diagnosis distribution of the radiation intensity of a reference surface from a desired distribution, expected within the model system, can indicate that the radiation power of the test beams does not correspond to the stipulations as early as when leaving the light source unit.

The diagnosis distribution of the radiation intensity secondly makes it possible to monitor the transmission of the optical elements of the optical system. A deviation of the spatial diagnosis distribution of the radiation intensity of a reference surface from a desired distribution can likewise indicate that the radiation power of the test beams has been attenuated in an unforeseen manner by at least one of the optical elements.

If it is assumed that the second case is present, then the spatial diagnosis distribution of the radiation intensity can be converted into a spatial diagnosis distribution of the transmission. The spatial diagnosis distribution of the transmission of a reference surface indicates what transmission the reference surface of the model system would have to have for the test beams such that the measured measurement values would arise. It is assumed, therefore, that any deviation of the measured radiation powers of the test beams is caused exclusively by a transmission distribution of the reference surface. The entire aberration of the optical system is therefore assigned to one reference surface.

According to the invention, the calculation of the spatial diagnosis distribution is carried out not just for one, but for a plurality of reference surfaces, it being assumed each time that only the respective reference surface is responsible for the deviation of the measurement values. The experienced user can then recognize, on the basis of their experience with the optical system, which of the calculated cases is more realistic and, consequently, which of the reference surfaces is actually responsible for the deviation of the measurement values.

In one developed embodiment, the spatial diagnosis distribution on a plurality of reference surfaces is determined simultaneously. It is therefore assumed that not just one reference surface is damaged, but rather a plurality of reference surfaces simultaneously. With the aid of matrix diagonalization methods, explained in association with the figures, the deviation of the measurement values is assigned simultaneously to a plurality of reference surfaces. This has the advantage that the decision as to which reference surface is substantially responsible for the deviations does not have to be taken by the user of the optical system, but rather can be determined in an automated manner.

Within the meaning of the present application, the transmission of an optical element is understood as a generic term for the effect of the optical element on the radiation power of the test beams. If the optical elements are a mirror, then this is understood to mean the reflectivity of the mirror for the test beams. In the case of lens elements, this is understood to mean the transmission for the test beams.

Analogously to the determination of the spatial diagnosis distribution of the radiation intensity of a reference surface, the spatial diagnosis distribution of the wavefront aberration of a reference surface can also be determined according to the invention. The measurement of the wavefront of the individual test beams is used to calculate the magnitude of the wavefront aberration of the test beams at the location of the reference surface. In a manner corresponding to the diagnosis distribution of the radiation intensity, a model system with a previously defined influence of the optical elements on the wavefront of the test beams is assumed in this case. The diagnosis distribution of the wavefront aberration of the reference surface thus indicates what wavefront aberration is present in the model system at each location of the reference surface. That is to say that it indicates what wavefront aberrations would be present at each location of the reference surface if the remaining components of the optical system had a previously defined influence on the wavefront aberration of the test beams. Therefore, it is assumed here, too, that any deviation of the measured wavefront aberrations of the test beams is caused exclusively by a figure deviation of the reference surface. The entire aberration of the optical system is therefore assigned to one reference surface. Therefore, the spatial diagnosis distribution of the wavefront aberration can be converted into a spatial diagnosis distribution of the figure deviation of the corresponding optical element.

The method according to the invention has the advantage that measurements are required only at one position, namely in the measurement plane of the optical system. Typically, this position can readily be attained also during the operation of the optical system in order to perform measurements there. According to the invention, these measurement values together with items of information about the arrangement of optical elements in the optical system which are contained in the impingement regions are sufficient to determine a spatial diagnosis distribution of at least one property of a reference surface. Typically, the reference surface is not readily accessible to measurements, since the optical system would have to be at least partly decomposed for this purpose. The method according to the invention therefore makes it possible to translate measurement values of a measurement variable at the location of the measurement plane to properties of a reference surface within the optical system. The method has the further advantage that the diagnosis distribution of a plurality of reference surfaces can be determined from the measurement values for the test beams. In this way, a plurality of spatial diagnosis distributions for different reference surfaces can be determined using only one measuring device at the location of the object field. This makes use of the fact that the test beams pass through the optical system on optical paths that differ in pairs, such that no two test beams cover the same optical path. As a result, the items of information about completely different optical paths are contained in the measurement values for the test beams. One example thereof is the amplitude of the radiation of each test beam, which contains the information about absorption along the optical path.

In one embodiment, the optical system comprises a projection lens, which images an object plane onto an image plane, and wherein the measurement plane corresponds to the image plane of the projection lens. In an alternative embodiment, the optical system comprises an illumination optical unit for illuminating an object plane, wherein the measurement plane corresponds to the object plane of the illumination optical unit. Both variants have the advantage that the measurement plane is particularly readily accessible. This holds true particularly when the projection lens and/or the illumination optical unit are/is arranged in a vacuum.

In some embodiments, the first measurement variable is identical to the second measurement variable. This facilitates the calculation of the diagnosis distribution, since the measurement values for different measurement regions can be better linked with one another.

The radiation can be the radiation from a light source unit which is used for operating the optical system. This has the advantage that the same boundary conditions as in the operation of the optical system are present. In particular, the method according to the invention can also be carried out within operating pauses in order to monitor the state of the optical system.

Alternatively, the radiation can be a measurement radiation specifically provided for the measurement. What is thereby achieved is that the measurement radiation can be conditioned in a targeted manner for the purposes of measurement with regard to spectrum and intensity distribution or angular distribution. Thus, by way of example, it is possible to carry out the measurement with radiation having different wavelengths. This has the advantage that different properties of the optical surfaces can be measured. Thus, the reflectivity of a mirror is dependent, for example, on the wavelength of the radiation used. Therefore, a plurality of measurements using radiation having different wavelengths enable the corresponding mirror surface to be tested more accurately, since not just the absolute change in a reflectivity is determined, but rather a change in the spectral profile.

In one developed embodiment, measurement values are detected not just at the location of a first and of a second measurement region, but at three or more measurement regions. In this case, each measurement region is likewise associated with a plurality of test beams which pass through the optical system on optical paths that differ in pairs and impinge on said measurement region at angles of incidence that differ in pairs with respect to the measurement plane. It is thereby possible to gather more information about the optical system, which leads to a more accurate spatial diagnosis distribution.

In one specific configuration, the at least one reference surface corresponds to a surface of an optical element of the optical system. This has the advantage that the spatial diagnosis distribution of the reference surface can be directly associated with physical properties of the optical element, such as, for example, a contamination distribution on the surface of the optical element.

In a further configuration, the optical system comprises an illumination optical unit having a collector mirror. In this case, a reflective surface of the collector mirror advantageously corresponds to the at least one reference surface. Since the collector mirror is arranged close to the source plasma, it is particularly susceptible to contaminations caused by the source plasma. For this reason, it is particularly important to determine a diagnosis distribution on the reflective collector surface.

In a further configuration, the at least one reference surface is a virtual surface corresponding to no surface of an optical element of the optical system. It is thereby possible also to assign effects that are not caused by surfaces of the optical system. Thus, to describe compaction of a lens element (densification of the lens element material on account of irradiation), it is possible to use a reference surface at the location of the lens element body. The reference surface then typically lies in the center of the lens element. Alternatively, it is also possible to use a virtual surface associated with no optical element. Thus, by way of example, it is possible to apply a virtual surface between the light source unit and the first optical element of the optical system. A reference surface of this type can advantageously be used in order to monitor variations in the spatial or spectral emission characteristic of the light source unit. By virtue of the fact that the reference surface does not correspond to the surface of the first optical element, effects which are caused by the light source unit and disturbances as a result of the first optical element can be better separated from one another.

In one embodiment, the entire radiation impinging at the location of the first measurement region is decomposed into the first plurality of test beams on the basis of its angles of incidence, and the entire radiation impinging at the location of the second measurement region is decomposed into the second plurality of test beams on the basis of its angles of incidence. This can be affected for example by the application of a raster in the angle space, such that each partial beam is defined as the totality of the radiation which impinges on the respective measurement region from the direction of a raster element in the angle space. In some configurations of the optical system, a natural decomposition on the basis of the angles of incidence into a plurality of test beams is already present. This is the case, for example, for reflective illumination optical units having a first optical element having first facet elements and a second optical element having second facet elements. In the case of illumination optical units of this type, the functioning of which is explained in connection with the figures, each second facet element corresponds exactly to an angle of incidence at the location of the object field. Consequently, the angular distribution at the location of the object field has disjoint angular areas respectively assigned to a second facet element. In such a case it is advantageous if the decomposition into test beams corresponds to the natural decomposition on account of the disjoint angular areas.

In one configuration of the method according to the invention, the measuring device measures the associated radiation power of the radiation of the test beam for each test beam of the first plurality and of the second plurality of test beams. Such a measurement is particularly simple to realize and makes it possible to calculate a spatial diagnosis distribution of the intensity. The calculation of a spatial diagnosis distribution of the intensity from the measurement values and the impingement regions for each test beam of the first plurality and of the second plurality of test beams has the advantage that the absorption at the corresponding reference surface can be deduced therefrom. As a result, it is then possible to determine, for example, the spatial distribution of a contamination on the reference surface.

Particularly in the cases in which the optical system comprises a projection lens and the measurement plane coincides with the image plane of the projection lens, it is furthermore advantageous if the test beams are parts of spherical-wave-like waves whose respective origin lies in an object plane assigned to the image plane. Such test beams can be provided for instance via a mask having punctiform test structures arranged thereon, such as, for instance, a perforated mask. The individual measurement regions from among those detected using the measuring device are then in each case images of the individual test structures. However, the test beams can also be provided via individual optical waveguides whose ends are arranged in the object plane of the projection lens.

Furthermore, it is advantageous if the measuring device has a wavefront measuring device. Such a wavefront measuring device can be used to measure phase and amplitude of arriving waves. These should be determinable at different angles relative to the measurement plane. In this case, the measurement can take place by interferometry, as is the case for example in a point diffraction interferometer (PDI), line diffraction interferometer (LDI) or a shearing interferometer such as, for instance, a lateral shearing interferometer (LSI). A wavefront measuring device can also be based on non-interferometric measuring methods, as in the case, for instance, of a Shack-Hartmann wavefront sensor. The wavefront measuring device used advantageously has a substrate, on which a shearing interferometer is applied by lithography. This brings about, for all field channels or pixels, the replication and shearing of the test beams advantageously present in the grating plane as convergently arriving spherical waves. Furthermore, the wavefront measuring device has a luminescence converter layer. Preferably, the measurement variable of the test beams that is determined using the measuring device comprises a phase of the respective test beam. Deviations of the wavefronts of the test beams from the desired wavefronts thereof can thus be determined. By making use of the method according to the invention, it is possible to determine the origin locations of individual wavefront deviations on at least one reference surface. By way of example, it is possible to determine therefrom a location on a lens element surface to which a specific wavefront deviation can be attributed. From this, it is possible to determine a figure deviation of said lens element surface, which, if appropriate, can be corrected in a correction step by the rework of the lens element surface.

It is furthermore advantageous if the measurement variable determined using the measuring device comprises a polarization state of the respective test beam. For this purpose, the measuring device should be embodied as a polarization measuring device. From the polarization states detected it is possible to deduce dichroism, retardation or rotation of the polarization at the individual reference surfaces.

In one specific configuration of the method according to the invention, the spatial diagnosis distribution of the radiation intensity on the at least one reference surface is calculated by a procedure in which an average radiation intensity is assigned to each impingement region, wherein the average radiation intensity of an impingement region is defined as the radiation power of the associated test beam at the location of the measurement region on which the test beam impinges, divided by the area content of the impingement region multiplied by a correction factor associated with said test beam, a plurality of points on the reference surface are defined or determined with the aid of a database, one or a plurality of impingement regions is or are assigned to each point of the plurality of points or an assignment of one or a plurality of impingement regions to each point is determined with the aid of a database, wherein an impingement region is deemed to be assigned to a point exactly when the point lies within the impingement region, a radiation intensity is assigned to each point of the plurality of points on the reference surface, which radiation intensity results as the sum of the average radiation intensities of the impingement regions which are assigned to the respective point.

In one embodiment, in this case the correction factor for each test beam is equal to one. This has the advantage that the concrete properties of the individual optical elements do not have to be determined in advance.

In an alternative embodiment, the correction factor for each test beam corresponds to the reciprocal of an attenuation experienced by the radiation power of the associated test beam along the optical path between the at least one reference surface and the measurement plane. What is thereby achieved is that a quantitative distribution of the intensity on the reference surfaces can be determined, such that the absolute radiation loading of the optical individual elements can be monitored on the basis of the diagnosis distribution.

In this case, it is advantageous, in particular, if the correction factors are determined in advance from the material properties and the optical design data of the optical system and are stored in a database. When carrying out the method, it is then possible to determine the correction factors for each test beam with the aid of a database. This accelerates the calculation of the spatial diagnosis distribution.

In one embodiment of the method according to the invention, the projection lens comprises a plurality of mirrors having optical surfaces and is designed for imaging radiation having a wavelength in the range of 5-15 nm. Projection lenses of this type are advantageously used in order to enable the imaging of particularly small structures.

In particular, the method according to the invention is developed in such a way that the optical system comprises an illumination optical unit having a plurality of mirrors having optical surfaces for illuminating an object field in the object plane with radiation having a wavelength in the range of 5-15 nm. Furthermore, the projection lens comprises a plurality of mirrors having optical surfaces and is designed for imaging radiation having a wavelength in the range of 5-15 nm. In this case, the illumination optical unit comprises at least one first mirror having a plurality of first facet elements and a second mirror having a plurality of second facet elements. Furthermore, each test beam of the first plurality of test beams and of the second plurality of test beams is reflected by exactly one first facet element and by exactly one second facet element along the optical path. In this case, the first facet element reflects the test beam in the direction of an assigned second facet element. This has the advantage that a natural decomposition of the radiation at the measurement regions into test beams is present. In particular, in this case the test beams associated with a measurement region are at a distance from one another in the angle space, as a result of which the detection of a measurement value is facilitated, since each ray registered by the measuring device can be unambiguously assigned to a test beam. A further advantage arises on account of the assignment of first facet elements to second facet elements. In order to achieve illumination of the second optical element that is as uniform as possible and hence an angular distribution of the radiation at the location of the object field that is as uniform as possible, at least some adjacent first facet elements are assigned to non-adjacent second facet elements. A mixing is achieved in this way, such that it is possible to provide a uniform angular distribution of the radiation at the location of the object field, even if the intensity distribution on the first optical element is non-uniform. However, this mixing also has the advantage according to the invention that effects which occur in the light path upstream of the first optical element can easily be distinguished from effects downstream of the first optical element. This is owing to the fact that the first optical element effects a discontinuous transformation of the radiation. Assuming that on or upstream of the first optical element a disturbance is present which has the effect that the intensity distribution on the first optical element is reduced in a contiguous area, then this leads to intensity distributions on the downstream mirrors which are reduced in many disjoint areas. Since it is very unrealistic that one of the downstream mirrors is damaged at many disjoint areas, with the aid of the diagnosis distributions it can easily be established whether the disturbance is present upstream or downstream of the first optical element.

According to a further formulation, the object is achieved by a non-transient computer-readable medium for operating a measuring system for an optical system, comprising computer program instructions for processing items of information about a first plurality of test beams of a radiation which pass through the optical system and in the process impinge on an identical first measurement region in a measurement plane, wherein the test beams of the first plurality of test beams pass through the optical system on optical paths that differ in pairs and impinge on the first measurement region at angles of incidence that differ in pairs with respect to the measurement plane, comprising computer program instructions for processing items of information about a second plurality of test beams of a radiation which pass through the optical system and in the process impinge on an identical second measurement region in the measurement plane, wherein the test beams of the second plurality of test beams pass through the optical system on optical paths that differ in pairs and impinge on the second measurement region at angles of incidence that differ in pairs with respect to the measurement plane, wherein the second measurement region differs from the first measurement region, comprising computer program instructions for determining associated impingement regions on at least one reference surface of the optical system, wherein the associated impingement region for each test beam of the first plurality of test beams and of the second plurality of test beams on at least one reference surface of the optical system is calculated or is determined with the aid of a database, and wherein the impingement region associated with a test beam is defined as the surface region of the at least one reference surface, on which radiation of the respective test beam impinges, comprising computer program instructions for reading in measurement values of a first measurement variable of the radiation impinging at the location of the first measurement region, comprising computer program instructions for reading in measurement values of a second measurement variable of the radiation impinging at the location of the second measurement region, comprising computer program instructions for determining and assigning an associated measurement value for each test beam of the first plurality of test beams, comprising computer program instructions for determining and assigning an associated measurement value for each test beam of the second plurality of test beams, comprising computer program instructions for generating a spatial diagnosis distribution of at least one property of the at least one reference surface from the measurement values and the impingement regions for each test beam of the first plurality and of the second plurality of test beams.

A computer program product of this type can be loaded into the main memory of a computer, thereby enabling the computer to calculate the spatial diagnosis distribution from the corresponding measuring values. The calculation of the diagnosis distribution and thus the computer program product have the advantages explained above in connection with the method.

In one embodiment, the optical system comprises a projection lens, which images an object plane onto an image plane, and wherein the measurement plane corresponds to the image plane of the projection lens. In an alternative embodiment, the optical system comprises an illumination optical unit for illuminating an object plane, and wherein the measurement plane corresponds to the object plane of the illumination optical unit. Both variants have the advantage that the measurement plane is particularly readily accessible. This holds true, in particular, when the projection lens and/or the illumination optical unit are/is arranged in a vacuum.

In some embodiments, the first measurement variable is identical to the second measurement variable. This facilitates the calculation of the diagnosis distribution, since the measurement values for different measurement regions can be better linked with one another.

In one specific configuration, the computer program product is equipped with
  computer program instructions for reading in angles of incidence and measurement values for the measurement variable of the entire radiation impinging at the location of the first measurement region,
  computer program instructions for reading in angles of incidence and measurement values for the measurement variable of the entire radiation impinging at the location of the second measurement region,
  computer program instructions for defining the first plurality of test beams on the basis of the angles of incidence read in,
  computer program instructions for defining the second plurality of test beams on the basis of the angles of incidence read in,
  computer program instructions for determining and assigning an associated measurement value for each test beam of the first plurality of test beams,
  computer program instructions for determining and assigning an associated measurement value for each test beam of the second plurality of test beams.

In one embodiment of the computer program product, the measurement variable is the radiation power of the impinging radiation. Furthermore, the computer program product contains computer program instructions for determining and assigning an associated measurement value for each test beam of the first plurality of test beams which determine the radiation power within each test beam of the first plurality of test beams and allocate it to the respective test beam as an associated measurement value. Likewise, the computer program product contains computer program instructions for determining and assigning an associated measurement value for each test beam of the second plurality of test beams which determine the radiation power within each test beam of the second plurality of test beams and allocate it to the respective test beam as an associated measurement value. A computer program product of this type can be used to determine a spatial diagnosis distribution of the radiation intensity on the reference surface.

In particular, the computer program product already comprises computer program instructions for generating a spatial diagnosis distribution of the radiation intensity on the at least one reference surface from the measurement values and the impingement regions for each test beam of the first plurality and of the second plurality of test beams.

In this case, the computer program instructions for generating the spatial diagnosis distribution of the radiation intensity can comprise, for example:
  sub-instructions which assign an average radiation intensity to each impingement region, wherein the average radiation intensity of an impingement region is defined as the radiation power of the associated test beam at the location of the measurement region on which the test beam impinges, divided by the area content of the impingement region multiplied by a correction factor associated with said test beam,
  sub-instructions for defining a plurality of points on the at least one reference surface or for determining the plurality of points with the aid of a database,
  sub-instructions which assign one or a plurality of impingement regions to each point of the plurality of points or determine an assignment of one or a plurality of impingement regions to each point with the aid of a database, wherein an impingement region is deemed to be assigned to a point exactly when the point lies within the impingement region,
  sub-instructions through which a radiation intensity is assigned to each point of the plurality of points on the at least one reference surface, which radiation intensity results as the sum of the average radiation intensities of the impingement regions which are assigned to the respective point.

In one embodiment, in this case the correction factor for each test beam is equal to one. This has the advantage that the concrete properties of the individual optical elements do not have to be determined in advance.

In an alternative embodiment, the correction factor for each test beam corresponds to the reciprocal of an attenuation experienced by the radiation power of the associated test beam along the optical path between the at least one reference surface and the measurement plane. What is thereby achieved is that it is possible to determine a quantitative distribution of the intensity on the reference surfaces, such that the absolute radiation loading of the optical individual elements can be monitored on the basis of the diagnosis distribution.

In this case, it is advantageous, in particular, if the correction factors are determined in advance from the material properties and the optical design data of the optical system and are stored in a database and the computer program product contains computer program instructions for determining the respective correction factors for each test beam with the aid of the database. This accelerates the calculation of the spatial diagnosis distribution.

In a further embodiment, the computer program product comprises
  computer program instructions for storing the spatial diagnosis distribution in a memory,
  computer program instructions for loading a spatial diagnosis distribution from a memory,
  computer program instructions for comparing a first diagnosis distribution with a second diagnosis distribution.

This has the advantage that the temporal change in the diagnosis distribution can be monitored. This enables good supervision of the temporal change in properties of the optical system. Thus, by way of example, it is possible to monitor the deposition of contamination on a surface of the optical system.

In particular, the computer program product comprises computer program instructions for storing a multiplicity of spatial diagnosis distributions in a database, the spatial diagnosis distributions being associated with different points in time. This makes it possible to analyze the temporal development of the spatial diagnosis distributions. The cause of the disturbance can likewise be deduced on the basis of the temporal development. While for example optical elements near a source plasma are contaminated rapidly, impurity particles deposit only slowly on optical elements that are further away. Therefore, the temporal development of the diagnosis distribution additionally allows the location of the disturbance to be delimited more closely.

Besides the direct calculation of the diagnosis distribution during the operation of the optical system, the program product according to the invention can also be used for the later analysis of recorded measurement data.

In particular, in this case, the computer program instructions for comparing a first diagnosis distribution with a second diagnosis distribution contain sub-instructions via which the ratio between the first and second diagnosis distributions is formed.

A microlithography projection exposure apparatus comprising a computer system comprising the computer program product described has the advantages explained above with regard to the computer program product.

The invention furthermore relates to a method for monitoring an optical system. In this case, the method for monitoring an optical system comprises the following steps:
  measuring the optical system in accordance with a method described above at a first point in time resulting in a first spatial diagnosis distribution and at a second point in time resulting in a second spatial diagnosis distribution,
  determining the temporal change between the first and second spatial diagnosis distributions.

This monitoring method has the advantage that it is possible to monitor temporal changes in properties of the optical system. Thus, by way of example, it is possible to monitor the deposition of contamination on a surface of the optical system.

In particular, the invention also relates to a method for monitoring an optical system and a light source unit, comprising the following steps:
  measuring the optical system in accordance with a method described above at a first point in time resulting in a first spatial diagnosis distribution,
  evaluating the spatial diagnosis distribution,
  readjusting a property of the light source unit, in particular switching off the light source unit, on the basis of the results of the evaluation of the spatial diagnosis distribution.

According to the invention, by way of example, the radiation loading at the location of the reference surface can be deduced from the spatial diagnosis distribution. If the result of the evaluation reveals that the radiation loading lies above a defined limit value, then the intensity of the light source unit can be reduced in order to prevent permanent damage to optical elements of the optical system.

Furthermore, the present invention relates to a method for monitoring an optical system and a light source unit. In this case, the light source unit provides radiation for operating the optical system. The method contains the following steps:
  measuring the optical system in accordance with the method described above at a first point in time resulting in a first spatial diagnosis distribution of a reference surface and a second point in time resulting in a second spatial diagnosis distribution of the reference surface, wherein the measurement of the optical system is carried out with the aid of the radiation of the light source unit,
  determining the temporal change between the first and second spatial diagnosis distributions,
  determining temporal changes in a spatial or spectral emission characteristic of the light source unit from the temporal change between the first and second spatial diagnosis distributions.

The light source unit can thereby be monitored without the aid of additional detectors. Furthermore, it is not necessary to separate the light source unit from the optical system, since the monitoring of the light source unit is carried out through the optical system, solely with the aid of measurement values at the location of the measurement regions.

In one specific configuration of the two monitoring methods described, the determination of the temporal change between the first and second spatial diagnosis distributions is effected by forming a ratio between the first and second diagnosis distributions.

The invention likewise relates to a method for correcting an optical system:
  measuring the optical system in accordance with one of the methods described above resulting in a first spatial diagnosis distribution of a reference surface,
  carrying out a correction step on the basis of the spatial diagnosis distribution of the reference surface.

The correction step can be, for example, the rework of a lens element surface in order to correct wavefront aberrations. Furthermore, such a correction step can be the cleaning of optical elements. Particularly when cleaning mirrors for the reflection of EUV radiation, atomic hydrogen is used. Such cleaning methods for eliminating contamination on mirrors for the EUV wavelength range are known from DE102008000551A1, for example. The correction step can accordingly be the start-up of such a hydrogen cleaning head. Alternatively or supplementarily, the correction step can be the displacement, tilting or deforming of optical elements by drivable manipulators.

BRIEF DESCRIPTION OF THE DRAWINGS

The invention is explained in greater detail with reference to the drawings.

FIG. 2a shows an illustration of a projection exposure apparatus comprising an illumination optical unit and a projection optical unit for use with EUV radiation.

FIG. 2b shows a plan view of the first optical element of the illumination optical unit according to FIG. 2a.

FIG. 2c shows a plan view of the second optical element of the illumination optical unit according to FIG. 2a.

FIG. 4a schematically shows the beam path of test beams through a projection lens.

FIG. 4b shows the ratio of two diagnosis distributions for a first reference surface of the projection lens according to FIG. 4a.

FIG. 4c shows the ratio of two diagnosis distributions for a second reference surface of the projection lens according to FIG. 4a.

FIG. 7a shows a further view of the projection exposure apparatus according to FIG. 2a, wherein individual test beams have been highlighted.

FIGS. 7b-7n show the impingement regions of four test beams on different reference surfaces.

FIGS. 8a to 8i show the diagnosis distribution of the radiation intensity on different reference surfaces.

FIGS. 9a to 9i illustrate the temporal change in the diagnosis distribution as a result of damage to one of the mirrors.

DETAILED DESCRIPTION OF PREFERRED EMBODIMENTS

Figure 1:
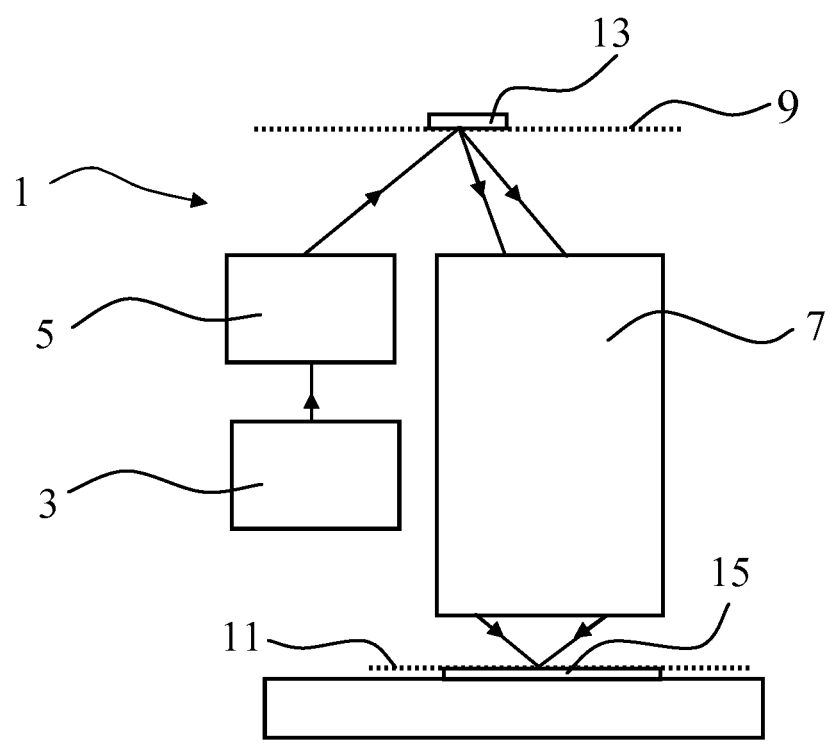
FIG. 1 shows a schematic illustration of a projection exposure apparatus comprising an illumination optical unit and a projection optical unit.

The reference signs have been chosen such that objects illustrated in FIG. 1 have been provided with one-digit or two-digit numbers. The objects illustrated in the further figures have reference signs having three or more digits, wherein the last two digits indicate the object and the preceding digit indicates the number of the figure in which the object is illustrated. Therefore, the reference numerals of identical objects which are illustrated in a plurality of figures correspond in terms of the last two digits. If appropriate, the description of these objects can be found in the text concerning a previous figure.

LIST OF REFERENCE SIGNS

1 Microlithography projection exposure apparatus
3 Light source unit
4 Radiation
5 Illumination optical unit
7 Projection lens
9 Object plane
11 Image plane/measurement plane
12 Image field
13 Structure-bearing mask
15 Substrate
17 First optical element
19 First facet elements
20 Intensity distribution
21 Second optical element
23 Second facet elements
25 First telescope mirror
27 Second telescope mirror
29 Diffraction mirror
31 Object field
33 First mirror of the projection lens
35 Second mirror of the projection lens
37 Third mirror of the projection lens
39 Fourth mirror of the projection lens
41 Fifth mirror of the projection lens
43 Sixth mirror of the projection lens
45 Optical axis
47 Source plasma
48 Collector mirror
49 Droplet generator
50 Laser
51 Opening in collector mirror
52 Intermediate focus
53 Entrance pupil plane
54 Chief ray
55 Lens element
56 Lens element
57 Lens element
58 Optical individual elements
59 Aperture stop
61 First measurement region
62 Second measurement region
63 Third measurement region
64a, b, c, d First plurality of test beams
65a, b, c, d Second plurality of test beams
66 First surface of the lens element 56
66a, b, c Regions on lens element surface 66
67a, d Impingement regions of two test beams
68a, d Impingement regions of two test beams
69 Measuring device
70 Measuring device
71 First surface of the lens element 57
71a-d Region on lens element surface
72a, d Impingement regions of two test beams
73a, d Impingement regions of two test beams
74 Test beam 1
75 Test beam 2
76 Illumination device
77 Test waves
78 Mask
79 Punctiform openings
80 Second surface of the lens element 56
81 Volume body of the lens element 56
82 Reference surface of the volume body of the lens element 56
83 Shearing grating
84 Luminescence converter layer
85 CCD detector
86 Computer system
87 Displacement devices
88 Individual rays
89a, b, c, d Impingement regions FIG. 1 shows a schematic illustration of a microlithography projection exposure apparatus 1. The microlithography projection exposure apparatus 1 comprises, inter alia, the light source unit 3 and the illumination optical unit 5 for illuminating an object field in the object plane 9, in which a structure-bearing mask 13 is arranged. A further part of the microlithography projection exposure apparatus 1 is a projection lens 7 for imaging the structure-bearing mask 13 onto a substrate 15, the so-called wafer. This substrate 15 contains a photosensitive layer, which is chemically altered during exposure. Then this is referred to as a lithographic step. In this case, the structure-bearing mask 13 is arranged in the object plane 9 and the substrate 15 is arranged in the image plane 11 of the projection lens 7. In this case, the illumination optical unit 5 and the projection lens 7 comprise a multiplicity of optical elements. These optical elements can in this case be embodied either in refractive fashion or in reflective fashion. Combinations of refractive and reflective optical elements within the illumination optical unit 5 or the projection lens 7 are also possible Likewise, the structure-bearing mask 13 can be embodied either in reflective fashion or in transmissive fashion. Such microlithography projection exposure apparatuses consist completely of reflective components particularly when they are operated with radiation having a wavelength of <193 nm, in particular having a wavelength in the range of 5 to 15 nm. Microlithography projection exposure apparatuses 1 are often operated as so-called scanners. That means that the structure-bearing mask 13 is moved through a slot-shaped illumination field along a scanning direction, while the substrate 15 is correspondingly moved in the image plane 11 of the projection lens 7. In this case, the ratio of the speeds of structure-bearing mask 13 and substrate 15 corresponds to the magnification of the projection lens 7, which is usually less than 1, in particular equal to ¼.

FIG. 2a shows one configuration of a microlithography projection exposure apparatus 201 comprising an illumination optical unit 205 and a projection lens 207. The illumination optical unit 205 in this case comprises a first optical element 217 having a plurality of reflective first facet elements 219 and a second optical element 221 having a plurality of second reflective facet elements 223. A first telescope mirror 225 and a second telescope mirror 227 are arranged in the light path downstream of the second optical element 221, said telescope mirrors both being operated with normal incidence, that is to say that the radiation impinges on both mirrors at an angle of incidence of between 0° and 45°. In this case, the angle of incidence is understood to be the angle between incident radiation and the normal to the reflective optical surface. A deflection mirror 229 is arranged downstream in the beam path and directs the radiation impinging on it onto the object field 231 in the object plane 209. The deflection mirror 229 is operated with grazing incidence, that is to say the radiation impinges on the mirror at an angle of incidence of between 45° and 90°. A reflective structure-bearing mask is arranged at the location of the object field 231, and is imaged into the image plane 211 with the aid of the projection lens 207. The projection lens 207 comprises six mirrors 233, 235, 237, 239, 241 and 243. All six mirrors of the projection lens 207 each have a reflective optical surface extending along a surface that is rotationally symmetrical about the optical axis 245.

Figure 2B:
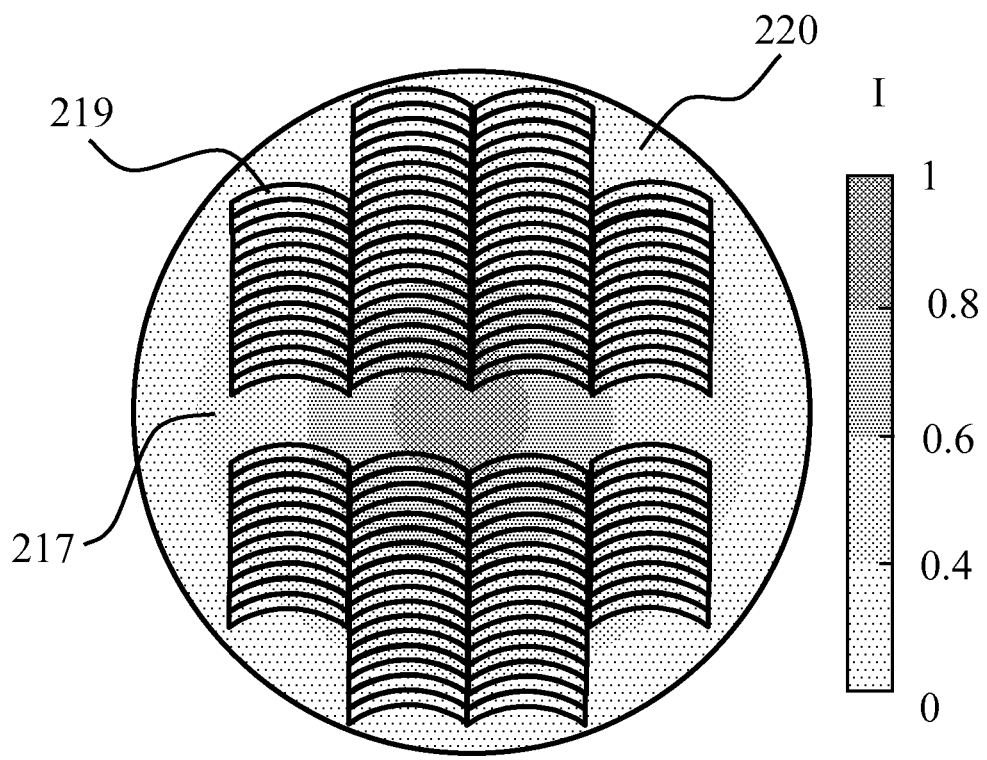

FIG. 2b shows a plan view of the first optical element 217, which comprises a plurality of first reflective facet elements 219. Each of the first reflective facet elements 219 has a reflective surface for reflecting the impinging radiation.

Figure 2C:
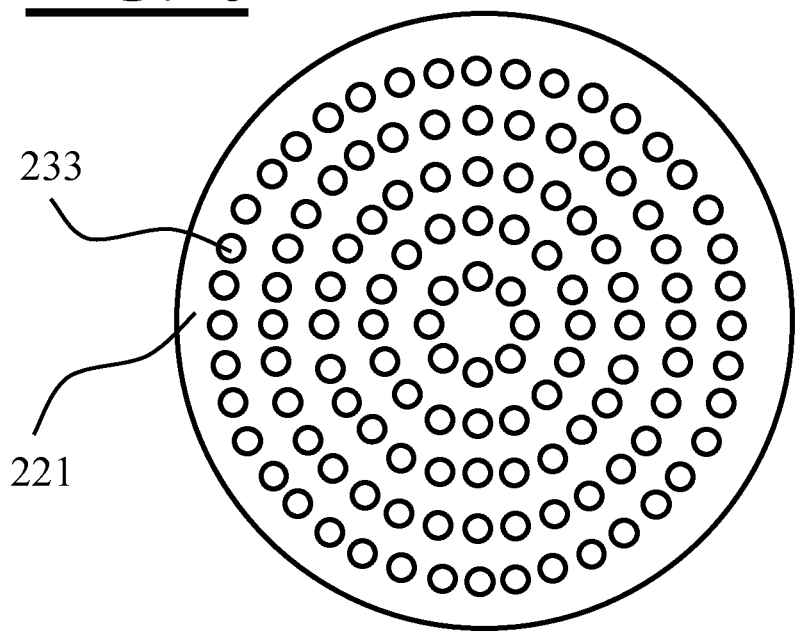

FIG. 2c shows a corresponding plan view of the second optical element 221 having a plurality of second reflective facet elements 223.

The microlithography projection exposure apparatus according to FIG. 2a furthermore comprises a light source unit 203, which directs radiation onto the first optical element 217. In this case, the light source unit 203 comprises a source plasma 247, which emits radiation in the wavelength range of 5-15 nm. A collector mirror 248 is used to collect the radiation of the source plasma. The light source unit 203 can be designed in various embodiments. A laser plasma source (LPP) is illustrated. With this type of source, a narrowly delimited source plasma 247 is generated by a small material droplet being produced by a droplet generator 249 and being brought to a predetermined location, where the material droplet is irradiated with a high-energy laser 250, such that the material undergoes transition to a plasma state and emits radiation in the wavelength range of 5 to 15 nm. In this case, the laser 250 can be arranged in such a way that the laser radiation falls through an opening 251 in the collector mirror 248 before it impinges on the material droplet. By way of example, an infrared laser having a wavelength of 10 μm is used as the laser 250. Alternatively, the light source unit 203 can also be embodied as a discharge source in which the source plasma 247 is generated with the aid of a discharge.

The radiation generated by the light source unit 203 then illuminates the first reflective optical element 217, where it generates an intensity distribution 220, which is illustrated in FIG. 2b. The intensity distribution 220 is approximately rotationally symmetrical and decreases from a center outward.

The collector mirror 248 and the first reflective facet elements 219 have an optical effect such that images of the source plasma 247 arise at the locations of the second reflective facet elements 223 of the second optical element 221. For this purpose, firstly the focal length of the collector mirror 248 and that of the first facet elements 219 are chosen in accordance with the spatial distances. This is done, for example, by providing the reflective optical surfaces of the first reflective facet elements 219 with suitable curvatures. Secondly, the first reflective facet elements 219 have a reflective optical surface with a normal vector whose direction defines the orientation of the reflective optical surface in space, wherein the normal vectors of the reflective surfaces of the first facet elements 219 are oriented in such a way that the radiation reflected by a first facet element 219 impinges on an assigned second reflective facet element 223. The optical element 221 is arranged in a pupil plane of the illumination optical unit 205, which is imaged onto the exit pupil plane with the aid of the mirrors 225, 227 and 229. In this case, the exit pupil plane of the illumination optical unit 205 corresponds exactly to the entrance pupil plane 253 of the projection lens 207. Consequently, the second optical element 221 lies in a plane that is optically conjugate with respect to the entrance pupil plane 253 of the projection lens. For this reason, the intensity distribution of the radiation on the second optical element 221 is in a simple relationship with the angle-dependent intensity distribution of the radiation in the region of the object field 231. In this case, the entrance pupil plane 253 of the projection lens 207 is defined as the plane perpendicular to the optical axis 245 in which the chief ray 254 intersects the optical axis 245 at the midpoint of the object field 231.

The task of the second facet elements 223 and of the downstream optics comprising the mirrors 225, 227 and 229 is to image the first facet elements 219 in a superimposing fashion onto the object field 231. In this case, superposing imaging is understood to mean that the images of the first reflective facet elements 219 lie in the object plane and at least partly overlap there. For this purpose, the second refractive facet elements 223 have a reflective optical surface with a normal vector whose direction defines the orientation of the reflective optical surfaces in space. For each second facet element 223, the direction of the normal vector is chosen such that the facet element 219 assigned to it is imaged onto the object field 231 in the object plane 209. Since the first facet elements 219 are imaged onto the object field 231, the form of the illuminated object field 231 corresponds to the outer form of the first facet elements 219. The outer form of the first facet elements 219 is therefore usually chosen to be arcuate such that the long boundary lines of the illuminated object field 231 run substantially arcuately about the optical axis 245 of the projection lens 207.

Figure 3:
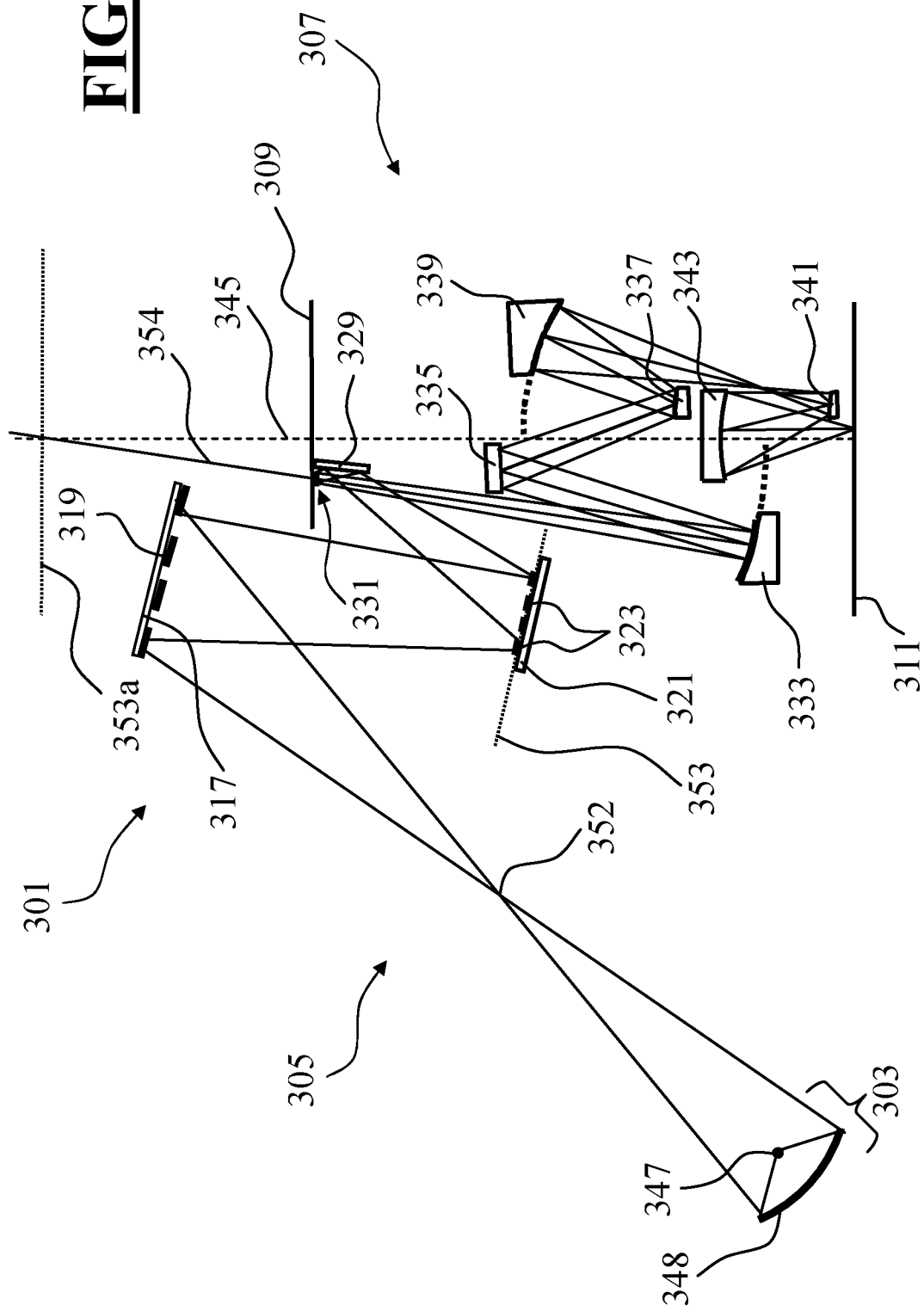
FIG. 3 shows a projection exposure apparatus comprising an alternative illumination optical unit and an alternative projection optical unit for use with EUV radiation.

FIG. 3 shows a further configuration of the microlithography projection exposure apparatus. In this case, the projection exposure apparatus 301 comprises the illumination optical unit 305 and the projection lens 307. In contrast to the projection lens 207 illustrated in FIG. 2a, the projection lens 307 according to FIG. 3 has a negative vertex focal length of the entrance pupil. That is to say that the entrance pupil plane 353 of the projection lens 307 is arranged in the light path upstream of the object field 331. If the chief ray 354 is extended further, without taking account of the reflection at the structure-bearing mask at the location of the object field 331, then the chief ray intersects the optical axis 345 in the plane 353a. If account is taken of the reflection at the structure-bearing mask at the location of the object field 331 and at the deflection mirror 329, then the plane 353a coincides with the entrance pupil plane 353. In the case of such projection lenses having a negative vertex focal length of the entrance pupil, the chief rays at different object field points at the location of the object field 331 have a divergent wave path in the light direction. Projection lenses of this type are known from US 2009/0079952A1.

A further difference with respect to the embodiment according to FIG. 2a is that here the source plasma 347 is firstly imaged onto an intermediate focus 352 with the aid of the collector mirror 348. Said intermediate focus 352 is then imaged onto the second reflective facet elements 323 of the second optical element 321 with the aid of the first reflective facet elements 319 of the first optical element 317.

FIG. 4 shows a schematic illustration of a projection lens 407 constructed from optical individual elements in the form of the lens elements 455, 456 and 457. The refractive illustration is purely by way of example. For the purposes of the invention, the optical individual elements can also be reflective or diffractive optical elements. During operation, the projection lens 407 images a structure-bearing mask 431 at the location of the object plane 409 onto the image plane 411. In the present embodiment, the image plane 411 corresponds to the measurement plane. For the purposes of measurement, the structure-bearing mask is typically replaced by an optical element without an optical effect such as, for example, a plane plate in the transmissive case, or by a plane mirror in the case of a reflective configuration. Alternatively, for the purposes of measurement, it is also possible to use a perforated mask or a reflective reticle having punctiform reflective structures. For this reason, the diffraction of the radiation at the structure-bearing mask need not be taken into account in the calculation of the impingement regions that is described below. The use of a perforated mask or of a reflective reticle having punctiform reflective structures additionally makes it possible to measure the projection lens with coherent spherical waves which have their midpoint at the point structures of the reticle.

The aperture of the projection lens 407 is delimited by the aperture stop 459. A first plurality of four test beams 464a, 464b, 464c, 464d of a radiation impinges at a first measurement region 461 in the measurement plane and image plane 411. The test beams 464a and 464d thereof have been hatched for the sake of better illustration. The four test beams 464a to 464d pass through the optical system on paths that differ in pairs, that is to say that there are no two test beams which pass through the optical system on the same path. Furthermore, the four test beams 464a to 464d impinge on the first measurement region at angles of incidence that differ in pairs with respect to the image plane. A second plurality of four test beams 465a, 465b, 465c and 465d impinges on a second measurement region 462. The test beams 465a and 465d thereof are identified by hatching. This second plurality of test beams 465a to 465d passes through the optical system likewise on paths that differ in pairs and impinges on the second measurement region at angles of incidence that differ in pairs with respect to the measurement plane. Four test beams likewise impinge on a third measurement region 463. The fact that the plurality of test beams for all three measurement regions in each case comprises exactly four test beams is only owing to the sake of better illustration. Any plurality of test beams can be used for the purposes of the invention.

According to a first embodiment, the optical system is divided into individual optical sections. In the example shown in FIG. 4a, each of the three lens elements 455, 456 and 457 is divided into three optical sections. This is shown by way of example on the middle lens element 456 of the projection lens in accordance with FIG. 4a. The latter has a first lens element surface 466, a second lens element surface 480 and a volume body 481. The two lens element surfaces 466 and 480 and the volume body 481 are in each case defined as an optical section. The same occurs for the remaining optical individual elements 455 and 457. In an alternative embodiment, an entire optical individual element 455, 456 and 457 can also be defined as an optical section or a group of optical individual elements taken together constitute such an optical section.

Furthermore, according to the first embodiment of the method according to the invention, a reference surface is assigned to each of the optical sections. In the case of the optical sections in the form of the lens element surface 466 and 480, the lens element surface 466 and 480 itself respectively serves as a reference surface. The optical section in the form of the volume body 481 is assigned a centroid surface of the volume body 481 that extends perpendicularly to the optical axis 445 as a reference surface 482.

For each of the test beams, an associated impingement region on each of the reference surfaces of the optical system is defined as the surface region of the reference surface on which radiation of the respective test beam impinges. Thus, the lens element 456 has for example a surface 466 on which an impingement region can be defined for each test beam. Thus, the test beam 464a impinges on the reference surface 466 and thereby defines the impingement region 467a. Correspondingly the test beam 464d likewise impinges on the reference surface 466 and thereby defines the impingement region 467d. The test beams 465a and 465d associated with the second measurement region 462 analogously define impingement regions on the reference surface 466. Thus, radiation of the test beam 465a impinges on the reference surface 466 within the impingement region 468a and radiation of the test beam 465d impinges on the reference surface 466 within the impingement region 468d. The position of the impingement regions on the reference surfaces can be determined from the design of the optical system with the aid of ray tracing.

469 designates a measuring device used to detect, for each of the four test beams 464a to 464d, an associated measurement value of a measurement variable of the test beam at the location of the first measurement region 461. 470 correspondingly designates a measuring device used to detect, for each test beam of the second plurality of test beams 465a to 465d, an associated measurement value of the same measurement variable at the location of the second measurement region 462.

The measuring devices 469 and 470 can be embodied for example in each case as a slot in the image plane 411 which only allows radiation of the respective measurement region 461 and 462 to pass through, in combination with spatially resolved radiation detectors (e.g. CCD detectors) arranged at a certain distance from the image plane 411. In the case of an arrangement of this type, radiation of different test beams impinges on different areas of the radiation detector, such that, for each test beam, a radiation power can be measured with the aid of the radiation detector. Alternatively, it is also possible to use a measuring optical unit, for example a Fourier optical unit, which converts angles in the measurement region into a position on the radiation detector.

By virtue of the fact that, for each test beam of the first plurality of test beams 464a to 464d and for each test beam of the second plurality of test beams 465a to 465d, both an associated measurement value and an associated impingement region on the reference surface 466 are known, it is then possible to calculate a spatial diagnosis distribution of at least one property of the reference surface 466. If the measurement variable is for example the radiation power of the radiation of the respective test beams, then it is possible to calculate a diagnosis distribution of the radiation intensity on the reference surface 466. Only the hatched test beams 464a, 464d, 465a and 465d are taken into account hereinafter. Valuable information about the state of the projection lens 407 can already be gathered from measurement values of these four test beams. For this purpose, an average radiation intensity is assigned to each of the impingement regions 467a, 467d, 468a and 468d. In this case, the average radiation intensity of an impingement region is defined as the radiation power of the associated test beam at the location of the measurement region on which the test beam impinges, divided by the area content of the impingement region multiplied by a correction factor associated with this test beam. In this case, the correction factor for each test beam corresponds for example to the reciprocal of an attenuation experienced by the radiation power of the associated test beam along the optical path between the reference surface 466 and the image plane. Since the test beams pass through the lens elements 456 and 457 on this path, an attenuation of the radiation intensity of the test beams takes place since the lens elements 456 and 457 have a certain absorption. Such an attenuation can be calculated on the basis of the known optical path and the material properties of the lens elements. The next step involves defining a plurality of points on the reference surface 466 or retrieving a predetermined plurality of points from a database. One or a plurality of impingement regions is or are then assigned to each point of this plurality of points, or an assignment of one or a plurality of impingement regions to each point is determined with the aid of a database. In this case, an impingement region is deemed to be assigned to a point exactly when the point lies within the impingement region. Accordingly, the impingement region 468a is assigned to a point which lies on the reference surface 466 within the impingement region 468a. Since the impingement regions 467a and 468d partly overlap, there are furthermore points on the reference surface 466 which lie within this overlap region. These points thus lie within the impingement region 467a and the impingement region 468d. They are assigned both impingement regions 467a and 468d. Next, a radiation intensity is assigned to each point of the plurality of points, which radiation intensity results as the sum of the average radiation intensities of the impingement regions which are assigned to the respective point. Therefore, for each point of the plurality of points on the reference surface 466 a radiation intensity at the location of the point is obtained. This diagnosis distribution of the radiation intensity obtained in this way can be compared with a desired distribution in order to check whether possible disturbances are present in the optical system or whether the radiation provided by a light source unit deviates from predetermined values. Returning to FIG. 2b, by way of example, it is possible to determine the intensity distribution 220 on the first optical element exclusively on the basis of measurement in the measurement regions. This has the advantage that the measurement regions are accessible in a simple fashion for a measurement. Since the microlithography projection exposure apparatus illustrated in FIG. 2a is operated in a vacuum, in order to avoid absorption of the EUV radiation, the surface of the first optical element 217 is not readily accessible for a measurement. However, according to the invention, the intensity distribution on the first optical element can be monitored using the measurements in the measurement regions.

In one developed embodiment of the invention, the optical system comprising the projection lens 407 is monitored by a diagnosis distribution being determined in accordance with the above method at a first point in time, and a second diagnosis distribution being determined at a second, later point in time. From the temporal change in the diagnosis distribution, it is then possible to draw conclusions about the type of disturbance in the optical system. If, by way of example, for the schematically depicted projection lens 407, the diagnosis distribution $I_1$ of the radiation intensity for the reference surface 466 and the reference surface 471, which corresponds to a first surface of the lens element 457, is determined at a first point in time and if the measurement and the calculation of the diagnosis distribution of the intensity on the reference surface 466 and the reference surface 471 are repeated again at a second, later point in time, such that a respective distribution $I_2$ is obtained, then changes in the optical system can be deduced from the temporal change between the first and second spatial diagnosis distributions. It is assumed that in the first measurement the same radiation power is in each case obtained for the hatched radiation beams 464a, 464d, 465a and 465d, whereas in the second measurement the radiation power of the radiation beams 464a and 465d has decreased to 50% of the original value. In the next step, it is assumed that this change occurs either as a result of damage to the reference surface 466 or as a result of damage to the reference surface 471, which has the effect that the respective reference surface has a lower transmission. Further causes of the change shall be ruled out for the moment. If the ratio of the second to the first diagnosis distribution on the reference surface 466 is then calculated, the curve illustrated in FIG. 4b arises. In the region 466a, corresponding to the impingement region 468a, the ratio is equal to one since the first and second diagnosis distributions in the impingement region 468a are identical. The same also applies to the region 466c, corresponding to the impingement region 467d. In the region 466b, by contrast, which corresponds to the two overlapping impingement regions 467a and 468d, the ratio is only 0.5 since the second measured radiation power of the radiation beams 464a and 465d corresponds only to half of the radiation power in the first measurement. The ratio of the diagnosis distributions on the reference surface 471, which is illustrated in FIG. 4c, arises correspondingly. In this case, the region 471a corresponds to the impingement region 472a, the region 471b corresponds to the impingement region 473a, the region 471c corresponds to the impingement region 472d, and the region 471d corresponds to the impingement region 473d. From the two curves in FIGS. 4b and 4c it is then possible to determine whether damage to the reference surface 466 or to the reference surface 471 is present. Assuming that the damage is on reference surface 466, then it is possible to deduce from FIG. 4b that the transmission of the reference surface 466 is reduced in the region 466b and thus in the overlapping impingement regions 467a and 468d. By contrast, if it is assumed that the damage is present on reference surface 471, then it would have to be deduced from FIG. 4c that reference surface 471 is damaged both in the region 471a and in the region 471d, whereas the reference surface 471 is still intact in the intervening regions 471b and 471c. Since it is relatively unlikely that contamination leading to a lower transmission will accumulate simultaneously at two different locations of a lens element, the scenario that the damage lies on reference surface 466 is more likely. Even the simple measurement of the radiation power of only four test beams at the location of the image plane 411 thus makes it possible to distinguish between these two scenarios. Even if only a likelihood statement can be made, a significantly more efficient elimination of disturbances is thereby made possible since the cause of a disturbance in the optical system can be delimited. In the present case, it is more likely that the performance of the system can be reestablished by cleaning the lens element surface 466 than by cleaning the lens element surface 471. As a result of such classification of the possible causes of disturbance according to their likelihood, more rapid repair is made possible.

In a further variant of the invention, the overlapping of the test beams at the reference surface and thus the overlapping of the impingement regions is additionally used to determine a further diagnosis distribution. For this purpose, at a first point in time, for each point on the reference surface to which two or more impingement regions are assigned, the average intensities of the test beams impinging there are determined. This is repeated at a later second point in time. In the next step, the ratio of the average radiation intensities of the impingement regions is determined. For each point in an overlap region, therefore, there are at least two ratios of radiation intensities. It is assumed that the cause of the temporal change is contamination on the reference surface in the overlap region. The ratios of the radiation intensities should then differ only slightly. This is owing to the fact that contamination in the overlap region has the same attenuating effect on all the test beams in the overlap region. If the ratios deviate greatly from one another, then this is an indication that the damage is not present on this reference surface, but rather in a region of the optical system in which the test beams do not overlap. If the standard deviation of the intensity ratios in all the overlap regions is thus determined as a diagnosis distribution, then a large standard deviation on the reference surface is a sign that this reference surface is not affected. The measurement accuracy of the measuring device is expediently used as a threshold value for the magnitude of the standard deviation.

Both impingement regions 467a and 468d are assigned to them. Next, a radiation intensity is assigned to each point of the plurality of points, which radiation intensity results as the sum of the average radiation intensities of the impingement regions which are assigned to the respective point.

In a further embodiment of the invention, a more detailed statement about the disturbance present is made by an aberration distribution being reconstructed on each reference surface. With the aid of this method, by way of example, the transmission of each optical surface can be determined in a spatially resolved fashion:

Step 1: firstly, a plurality N of test beams is in each case defined for a plurality M of measurement regions.

Step 2: for each test beam, the radiation powers are measured at a point in time $t_1$ at the location of the image plane. The measurement values $S_{mn}^{t1}$ are thus obtained. A vector $\vec{S}$ having Q=M·N entries is formed therefrom. Each entry $S_k^{t1}$: where k∈1, ..., M·N is associated with one of the test beams.

Step 3: each of the test beams passes through a plurality of reference surfaces 1, ..., F on the path through the optical system. At each of these reference surfaces, the test beam experiences an attenuation since the transmission is generally not optimal. The attenuation of the k-th test beam at the reference surface f where f∈1, ..., F at the point in time $t_1$ is designated by $T_{fk}^{t1}$. For the radiation power of the k-th test beam the following thus holds true:

$$S_k^{t1} = \Pi_{f=1}^{F} T_{kf}^{t1} \cdot S_{k0} \tag{1}$$

Where $S_{k0}$ designates the entrance radiation power of the k-th test beam.

Step 4: the measurement of the radiation power is then repeated at a later point in time $t_2$ with the same entrance radiation power. At this point in time, the following thus likewise arises:

$$S_k^{t2} = \Pi_{f=1}^{F} T_{kf}^{t2} \cdot S_{k0} \tag{2}$$

If the ratio of the two radiation powers is then formed, the following thus arises:

$$S_k' = \prod_{f=1}^{F} T_{kf}' \text{ where } S_k' = \frac{S_k^{t2}}{S_k^{t1}} \text{ and } T_{kf}' = \frac{T_{kf}^{t2}}{T_{kf}^{t1}} \tag{3}$$

$T'_{kf}$ thus describes the change in the transmission at the reference surface f between the first and second measurements for the k-th test beam.

Step 5: by forming the logarithm on both sides of the equation, this product can be converted into a sum. This gives rise later to linear equation systems, which are computationally simpler to handle.

$$s_k = \sum_{f=1}^{F} t_{kf} \text{ where } s_k = \ln(S_k') \text{ and } t_{kf} = \ln(T_{kf}') \tag{4}$$

Step 6: next, the change in transmission of the reference surface f is described by an initially unknown function to be $w_f(s_f, t_f)$. In this case, $(s_f, t_f)$ denote the coordinates of a point on the reference surface f. Physically, $w_f(s_f, t_f)$ corresponds to the logarithm of the change in transmission between the point in time $t_2$ and the point in time $t_1$ as a function of the location $(s_f, t_f)$ on the reference surface f.

$$w_f(s_f, t_f) = \ln\left(\frac{T_f^{t2}(s_f, t_f)}{T_f^{t1}(s_f, t_f)}\right) \tag{5}$$

where $T_f^{t1}(s_f, t_f)$ describes the transmission of the reference surface f at the location $(s_f, t_f)$ at the point in time $t_1$. The unknown function $w_f(s_f, t_f)$ thus characterizes the disturbance on the reference surface f.

Step 7: in order to determine the function $w_f(s_f, t_f)$, the latter is expanded according to a function system $\phi_p(S_f, t_f)$ where p∈1, ..., P.

$$w_f(s_f, t_f) = \sum_{p=1}^{P} c_p^f \phi_p(s_f, t_f) \tag{6}$$

Step 8: returning to formula (4), it now holds true that $t_{kf}$=ln $(T'_{kf})$ is identical to the averaging of the function $w_f(s_f, t_f)$ over the impingement region of the k-th radiation beam on the reference surface f.

$$t_{kf} = \frac{\int_{A_k^f} w_f(s_f, t_f) ds_f dt_f}{\int_{A_k^f} ds_f dt_f} \tag{7}$$

where $A_k^f$ designates the impingement region of the radiation beam k on the reference surface f. Therefore, the denominator of equation (7) corresponds to the area content of the impingement region $A_k^f$.

Step 8:
Inserting equation (6) into equation (7) yields:

$$t_{kf} = \sum_{p=1}^{P} c_p^f \frac{\int_{A_k^f} \phi_p(s_f, t_f) ds_f dt_f}{\int_{A_k^f} ds_f dt_f} \quad (8)$$

Figure 4D:
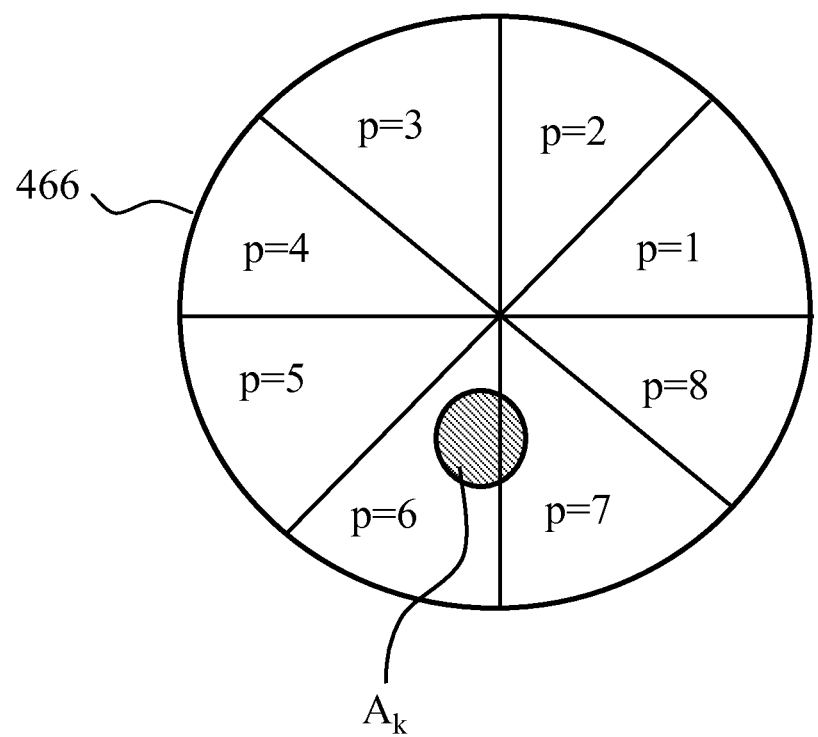
FIG. 4d shows the division of a reference surface into different regions.

The coefficients $$\phi_{kp}^f = \frac{\int_{A_k^f} \phi_p(s_f, t_f) ds_f dt_f}{\int_{A_k^f} ds_f dt_f} \quad (9)$$

are independent of the measurement values and are exclusively determined from the geometry of the optical system via the impingement regions and the choice of the function system $\phi_p (s_f, t_f)$. One very simple possibility for a function system is the division of the reference surface f into P different regions. This is shown in FIG. 4d. The reference surface is subdivided into the regions 1, . . . , 8, which define eight functions by:

$$\phi_p(s_f, t_f) = \begin{cases} 1 & \text{if } (s_f, t_f) \text{ within the area } p \text{ according to FIG. 4d} \\ 0 & \text{otherwise} \end{cases} \quad (10)$$

For the impingement region $A_k$ illustrated in FIG. 4d, the following thus arises:

$\phi_{k1}=0$ $\phi_{k2}=0$ $\phi_{k3}=0$ $\phi_{k4}=0$ $\phi_{k5}=0$ $\phi_{k6}=0.8$ $\phi_{k7}=0.2$ $\phi_{k8}=0$ (11)

This means nothing more than 80% of the impingement region $A_k$ lies within the area p=6, and 20% within the area p=7. Such a function system is particularly well suited if the expected disturbance is spatially highly localized, such as in the case of contaminants, for example.

Step 9: next, equation (8) is inserted into equation (4):

$$s_k = \sum_{f=1}^{F} \sum_{p=1}^{P} c_p^f \frac{\int_{A_k^f} \phi_p(s_f, t_f) ds_f dt_f}{\int_{A_k^f} ds_f dt_f} = \sum_{f=1}^{F} \sum_{p=1}^{P} c_p^f \phi_{kp}^f \quad (12)$$

By introducing the vectors $$\vec{c} = (c_1^1, \ldots, c_P^1, c_1^2, \ldots, c_P^2, \ldots, c_1^F, \ldots, c_P^F) \quad (13)$$

$$\vec{s} = (s_1, \ldots, s_Q) \quad (14)$$

and the matrix $$\phi = \begin{pmatrix} \phi_{11}^1 & \cdots & \phi_{1P}^1 & \phi_{11}^2 & \cdots & \phi_{1P}^2 & \cdots & \phi_{11}^F & \cdots & \phi_{1P}^F \\ \vdots & & \vdots & \vdots & & \vdots & & \vdots & & \vdots \\ \phi_{k1}^1 & \cdots & \phi_{kP}^1 & \phi_{k1}^2 & \cdots & \phi_{kP}^2 & \cdots & \phi_{k1}^F & \cdots & \phi_{kP}^F \\ \vdots & & \vdots & \vdots & & \vdots & & \vdots & & \vdots \\ \phi_{Q1}^1 & \cdots & \phi_{QP}^1 & \phi_{Q1}^2 & \cdots & \phi_{QP}^2 & \cdots & \phi_{Q1}^F & \cdots & \phi_{QP}^F \end{pmatrix} \quad (15)$$

the following equation system is obtained:

$$\vec{s} = \phi \cdot \vec{c} \quad (16)$$

Where the vectors $\vec{s}$ is determined by the measurement values and the matrix $\phi$ is dependent only on the geometry of the optical system, that is to say on the impingement regions and the function system. The unknown properties of the reference surfaces are contained in the vector $\vec{c}$. The numerical solution to this equation $\vec{c}$ corresponds, finally, to the tomographic reconstruction. Least square minimization results in the following solution:

$$\vec{c}_{LSQ} = (\phi^T \phi)^{-1} \phi^T \cdot \vec{s} \quad (17)$$

Inserting this solution into equation (6) yields the spatial distributions of the disturbances $w_f(s_f, t_f)$ which describe, for example, the contamination on the reference surfaces.

Figure 5B:
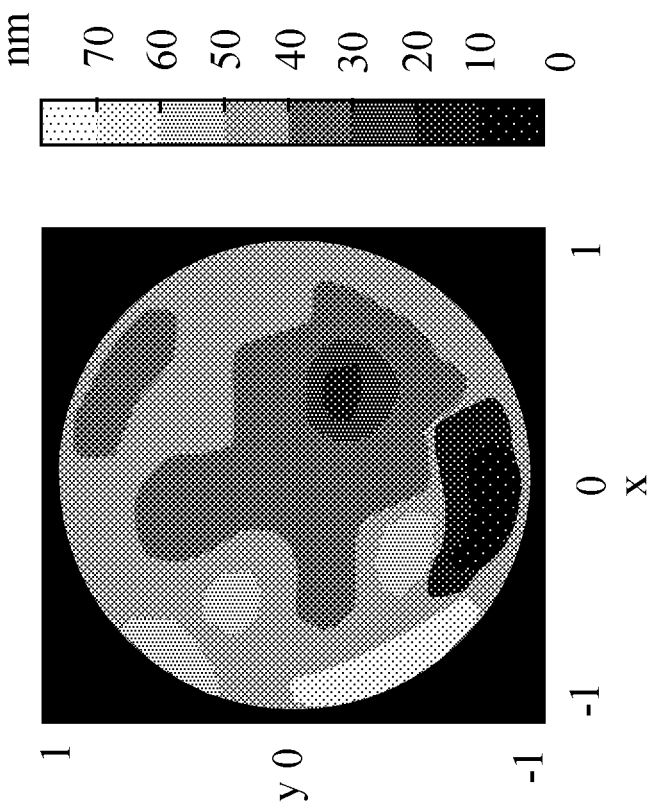
FIG. 5b shows a pupil aberration distribution for wavefront aberrations.
Figure 5A:
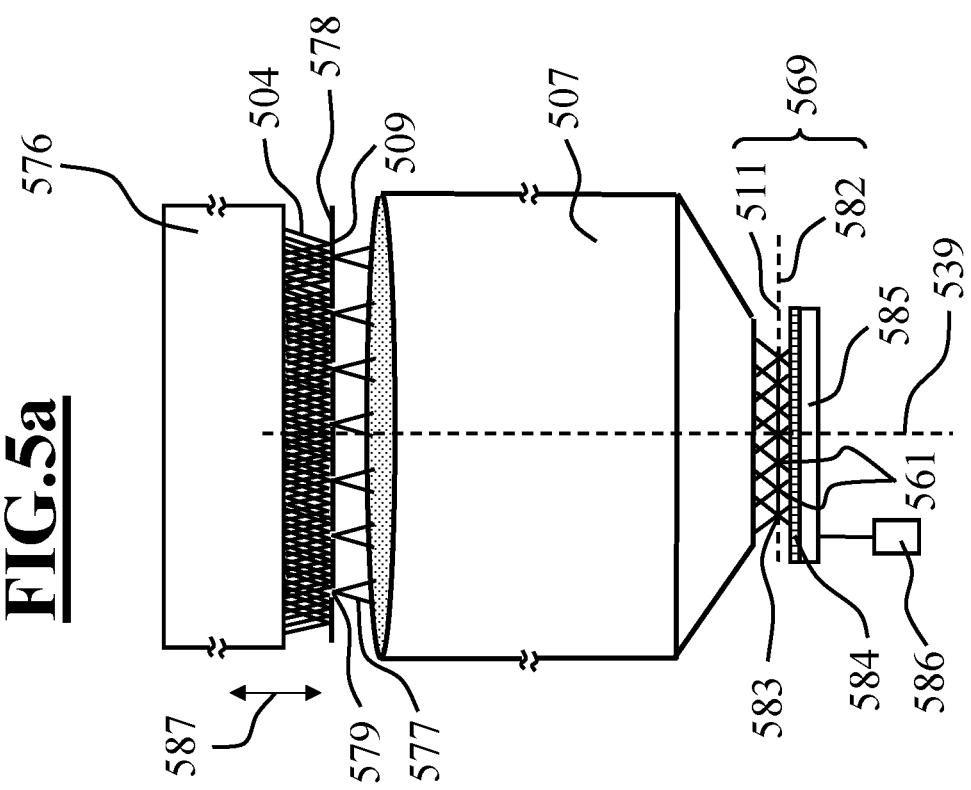
FIG. 5a shows a further schematic illustration of a microlithography projection exposure apparatus.

FIG. 5a illustrates a microlithography projection exposure apparatus 501. The illustrations in FIGS. 4a and 5a differ from one another to the effect that they each highlight different details of the exposure apparatus. The exposure apparatus 501 can be embodied as a stepper or as a scanner and is preferably operated with an illumination wavelength in the UV range, for example at 248 nm, 193 nm or 157 nm. Furthermore, the exposure apparatus 501 can also be designed for exposure using EUV radiation, that is to say using a radiation having a wavelength in the range of 5-15 nm. The microlithography projection exposure apparatus 501 has an optical system comprising a projection lens 507. A measuring device 569 for measuring the projection lens 507 is provided at the projection lens 507.

An illumination device 576 comprising a light source unit and an illumination optical unit is furthermore illustrated. The illumination device can be the same illumination device that is used for the operation of the microlithography projection exposure apparatus, or else a specifically designed illumination device provided for measuring the optical system. The illumination device 576 comprises a light source unit for generating electromagnetic test waves 577 in the form of spherical waves. The illumination device 576 generates coherent monochromatic electromagnetic radiation 504 in the form of UV light having, for example, a wavelength of 248 nm, 193 nm, 157 nm or a wavelength in the EUV range of 5-15 nm. The illumination device 576 furthermore comprises a mask 578 having punctiform structures, said mask being arranged in an object plane 509 of the projection lens 507. In the exemplary embodiment shown, the mask 578 is embodied as a perforated mask having a multiplicity of punctiform openings 579. The electromagnetic radiation 504 impinges on the mask 578 and is converted into the spherical test waves 577 by said mask. The individual test waves 577 pass through the projection lens 507 in optical paths that differ from one another.

The measuring device 569 has a detection surface. The detection surface is arranged in an image plane 511 of the projection lens 507, said image plane being assigned to the object plane 509. The individual test waves 577 are focused onto the respective measurement regions 561 in the image plane 511. The measuring device 569 is designed to measure a measurement variable of the test waves 577 at the location of the respective measurement regions 561 at different angles of incidence with respect to the image plane 511. The measurement variable can be, in principle, by way of example, the radiation power, a polarization state or the amplitude or phase of the incident test waves 577. In the exemplary embodiment illustrated in FIG. 5a, the measuring device 569 is embodied as a wavefront measuring device. The latter comprises a shearing grating 583 applied lithographically on the top side of a substrate, said grating bringing about, for all the measurement regions, the replication and the shearing of the spherical test waves 577 arriving convergently in the grating plane. During passage through the substrate, the original and the replicated (sheared) wavefronts diverge and finally impinge on a luminescence converter layer 584, where they interfere and become visible as shearing interferograms. A CCD detector 585 is arranged below the luminescence converter layer and, during operation, records the shearing interferograms in parallel simultaneously for all the measurement regions 561.

For each of the measurement regions 561, the respective phase of the test beams contained in the corresponding test wave 577 is measured by the measuring device 569 in accordance with FIG. 5a. In other words, the phase is measured for the different angles of incidence of the test waves 577 impinging on the detection surface of the measuring device 569 at respective measurement regions 561. From deviations of the measurement values from predetermined desired values, a pupil aberration distribution for wavefront aberrations such as are illustrated by way of example in FIG. 5b is determined for each measurement region 561. A total aberration distribution of the phase depending on the measurement regions 561 and the angle of incidence with respect to the image plane 511 results from the individual pupil aberration distributions at the different measurement regions 561. From the total aberration distribution and the impingement regions determined in the manner described above, individual aberration distributions are calculated for the individual optical sections using algorithmic reconstruction. This calculation is carried out in a computer system 586 and is described in detail below.

The individual aberration distributions determined in this way indicate the contribution of the respective optical section to the total aberration distribution in a manner spatially resolved over the respective reference surface of the relevant optical section. As a result, the origin of phase aberrations in the projection lens 507 can thus be accurately localized. The individual aberration distribution of the phase of, for example, the lens element surface 466 according to FIG. 4a indicates corresponding deviations of the surface from its desired surface. These deviations can thereupon be corrected by a correction step such as, for example, the rework of the lens element surface 466.

In accordance with a further embodiment of the method according to the invention, the individual aberration distributions are determined firstly for a first boundary condition and thereupon for a second boundary condition. From the individual aberration distributions determined, improved individual aberration distributions are thereupon determined for each optical section. Changing the boundary condition from the first to the second boundary condition can comprise various measures, some of which are indicated graphically in FIG. 4a. Thus, for instance, optical individual elements 465, 466, 467 can be displaced, tilted or rotated in a defined manner. Moreover, an optical individual element 465 can be deformed. The above-mentioned displacements of optical individual elements are advantageously performed transversely with respect to the optical axis 445. Corresponding displacement devices 487 are indicated with arrows in FIG. 4a. Furthermore, changing the boundary condition can comprise displacing the radiation source 576 along the optical axis 545. The corresponding displacement direction 587 is indicated by a further arrow in FIG. 5a.

Furthermore, changing the boundary condition from the first boundary condition to the second boundary condition can comprise changing a refractive index of a purge gas arranged between the optical individual elements 465, 466, 467. For this purpose, it is possible to change, for instance, the pressure of the purge gas via a feed device for the purge gas. Furthermore, the measurements can be effected with different refractive indices of a liquid film arranged between the projection lens 507 and the image plane 511. Furthermore, changing the boundary condition can consist in changing the electromagnetic test waves 577, such as, for instance, the wavelength of the test waves 577.

Furthermore, the measurements can be carried out for different positions of a sensor of the measuring device 569 in the image plane and/or different tilt positions relative to the optical axis 545. Changing the boundary condition can also comprise changing a temperature of at least one optical individual element 465, 466, 467 or introducing an additional optical element, in particular a phase plate, an absorption element and/or a polarizer into the beam path of the test waves 577.

The algorithmic reconstruction of an aberration distribution will be explained again below in association with FIG. 6; this time on the basis of the example of a phase distribution.

Figure 6:
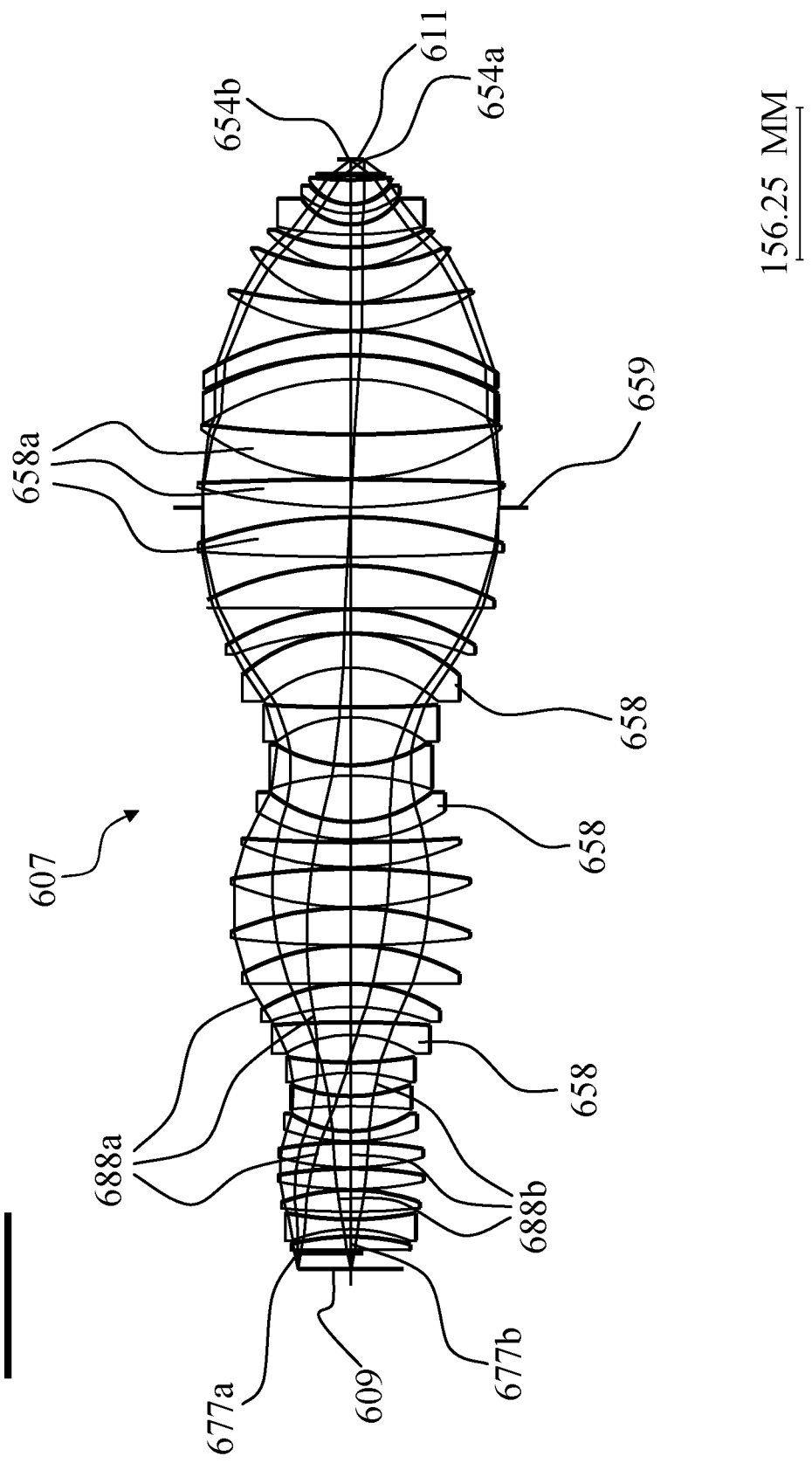
FIG. 6 shows a purely refractive projection lens.

FIG. 6 illustrates by way of example radiation paths of a first test wave 677a and of a second test wave 677b through an optical system in the form of a typical refractive projection lens 607 for microlithography. A projection lens of this type comprises a multiplicity of optical individual elements 658 in the form of lens elements. Three individual rays 688a and 688b are respectively depicted for each of the test waves 677a and 677b.

Optical individual elements 658a near the pupil are situated in the region of the aperture stop 659. As can be seen from FIG. 6, the beam paths of the two test waves 677a and 677b through the optical individual elements 658a near the pupil hardly differ. It is therefore advantageous according to the invention to combine the optical individual elements 658a near the pupil to form an optical section having a reference surface in the implementation of the method according to the invention.

A detailed description is given below of the computation algorithm according to the invention which is used to determine the individual aberration distributions for the individual optical sections from the total aberration distribution and the impingement regions on the individual reference surfaces of the optical sections. According to the invention, the computation algorithm is implemented in a computer program product. This means that the computer program product can be loaded into the main memory of a computer system, thereby enabling the computer system to execute the algorithm. The computation algorithm uses spline functions for the tomographic reconstruction of the projection lens 607.

The total aberration distribution of the phases is designated as the phase aberration map $W(x, y; \zeta, \eta)$. In this case, x and y denote the spatial coordinates of the measurement regions 654a and 654b in the image plane 611 and $\zeta$ and $\eta$ denote the angular coordinates of the measured test beams with respect to the image plane 611.

The phase aberration map $W(x, y; \varsigma, \eta)$ is assembled through linear superimposition corresponding to $$W(x, y; \varsigma, \eta) = \sum_{f=1}^{F} w_f(s_f(x, y; \varsigma, \eta), t_f(x, y; \varsigma, \eta))$$

from the contributions $w_f$ of the individual reference surfaces or system surfaces, which are consecutively numbered by the index f. In this case, the relation between the parameters (x, y; $\varsigma$, $\eta$) of an individual ray 688a, 688b and its point of intersection or intersection points $\vec{v}_f = (s_f, t_f)$ on the respective reference surfaces, which, for their part, are described in terms of their specific and adapted coordinates, is known very accurately as a result of the computational ray tracing.

As the next step, the surface aberrations are represented as a superimposition of contributions of the form $$w_f(s_f, t_f) = \sum_{p=1}^{P} c_p^f \phi_p(\tilde{v}_p^f) \text{ where } \tilde{v}_p^f = \sqrt{\left(\vec{V}_f - \vec{V}_p^f\right)^2 + \beta_f^2} \quad (19)$$

In this case, $c_p^f$ denote the expansion coefficients with regard to a raster-specific spline function system which is specified via the choice of the radial function $\phi(\tilde{v})$ and its spanning by a set of interpolation points $\{\vec{v}_p, p=1, 2, 3, \ldots, P\}$ adapted to the symmetry conditions. In this case, the function system can be chosen differently with regard to each reference surface. For this reason, the functions and their parameters are additionally provided with the index f. A radial displacement $\beta$ is also permitted as a further degree of freedom for such a description. As radial functions, a series of possibilities (in addition to others) are available for selection which differ with regard to their continuity and approximation properties:

biharmonic (thin plate): $\phi(v) = v^2 \ln(v), \beta^2 \geq 0$ triharmonic: $\phi(v) = v^4 \ln(v), \beta^2 \leq 0$ multiquadratic: $\phi(v) = v, \beta^2 \geq 0$ inverse multiquadratic: $\phi(v) = v^{-1}, \beta^2 \geq 0$ \quad (20)

but generally yield comparably usable spline approximations.

Next, a plurality of N test beams is in each case defined for a plurality M of measurement regions $B_1, \ldots, B_M$. For the measurement region $B_m$ where $m \in 1, \ldots, M$, these are the test beams $T_1^m, \ldots, T_N^m$.

Step 2: for each test beam $T_n^m$ where $m \in 1, \ldots, M$ and $n \in 1, \ldots, N$, the phase values are measured at the location of the associated measurement region. The measurement values $W_{mn}$ are thus obtained. A vector $\vec{W}$ having $Q = M \Box N$ entries is formed therefrom. Each entry $W_k$ where $k \in 1, \ldots, M \Box N$ is associated with one of the test beams $T_k$.

The phase measurement values $W_k$ for a test beam $T_k$ are defined by the average values of the phase over the associated measurement region and the associated solid angle range of the test beam.

$$w_k = \frac{\int_{\tilde{T}_k} dx\, dy\, d\varsigma\, d\eta\, W(x, y; \varsigma, \eta)}{\int_{\tilde{T}_k} dx\, dy\, d\varsigma\, d\eta} \quad (21)$$

Typically, measurement region and solid angle range of the test beam $T_k$ are predetermined by the area extents of the detector elements in the field or pupil space.

Likewise, the contribution of the reference surface f to the phase aberration $w_{kf}$ corresponds to the averaging of the function $w_f(s_f, t_f)$ over the impingement region of the k-th radiation beam on the reference surface f.

$$w_{kf} = \frac{\int_{A_k^f} w_f(s_f, t_f)\, ds_f\, dt_f}{\int_{A_k^f} ds_f\, dt_f} \quad (22)$$

where $A_k^f$ denotes the impingement region of the radiation beam k on the reference surface f. Therefore, the denominator of the equation (22) corresponds to the area content of the impingement area $A_k^f$.

Inserting equation (19) into equation (22) yields:

$$w_{kf} = \sum_{p=1}^{P} c_p^f \frac{\int_{A_k^f} \phi_p(s_f, t_f)\, ds_f\, dt_f}{\int_{A_k^f} ds_f\, dt_f} \quad (23)$$

The coefficients $$\phi_{kp}^f = \frac{\int_{A_k^f} \phi_p(s_f, t_f)\, ds_f\, dt_f}{\int_{A_k^f} ds_f\, dt_f} \quad (24)$$

are independent of the measurement values and are determined exclusively from the geometry of the optical system by the impingement regions and the choice of the function system $\phi_p(s_f, t_f)$.

The total phase aberration $W_k$ of a test beam $T_k$ results from the sum of the phase aberrations at the f reference surfaces $w_{kf}$ $$W_k = \sum_{f=1}^{F} w_{kf} \quad (25)$$

Inserting equation (23) into (25) yields:

$$W_k = \sum_{f=1}^{F} \sum_{p=1}^{P} c_p^f \frac{\int_{A_k^f} \phi_p(s_f, t_f)\, ds_f\, dt_f}{\int_{A_k^f} ds_f\, dt_f} = \sum_{f=1}^{F} \sum_{p=1}^{P} c_p^f \phi_{kp}^f \quad (26)$$

After performing the integration in equation (21) and (24) over the surface elements known from the sensor layout and ray tracing and a corresponding unambiguous arrangement of the measurement values $W_k$ and the coefficients $c_p^f$ to form column vectors, the linear equation system once again arises:

$$\vec{W} = \phi \cdot \vec{c} \quad (27)$$

with the corresponding vectors $$\vec{c} = (c_1^1, \ldots, c_p^1, c_1^2, \ldots, c_p^2, \ldots, c_1^F, \ldots, c_p^F) \quad (28)$$

$$\vec{W} = (W_1, \ldots, W_Q) \quad (29)$$

and the matrix $$\phi = \begin{pmatrix} \phi_{11}^1 & \cdots & \phi_{1P}^1 & \phi_{11}^2 & \cdots & \phi_{1P}^2 & \cdots & \phi_{11}^F & \cdots & \phi_{1P}^F \\ \vdots & & \vdots & \vdots & & \vdots & & \vdots & & \vdots \\ \phi_{k1}^1 & \cdots & \phi_{kP}^1 & \phi_{k1}^2 & \cdots & \phi_{kP}^2 & \cdots & \phi_{k1}^F & \cdots & \phi_{kP}^F \\ \vdots & & \vdots & \vdots & & \vdots & & \vdots & & \vdots \\ \phi_{Q1}^1 & \cdots & \phi_{QP}^1 & \phi_{Q1}^2 & \cdots & \phi_{QP}^2 & \cdots & \phi_{Q1}^F & \cdots & \phi_{QP}^F \end{pmatrix} \quad (30)$$

The numerical solution to equation (27) corresponds, finally, to the tomographic reconstruction which allows the spline contributions of the individual system surface to be deduced from the measured phase delays. Least square minimization yields the following solution:

$$\vec{c}_{LSQ} = (\phi^T \phi)^{-1} \phi^T \cdot \vec{W} \quad (31)$$

The inversion of the symmetrical dim($\underline{c}$)×dim($\underline{c}$) normal matrix $N = (\phi^T \phi)$ can be effected for example by its diagonalization. This gives rise to the representation $$N = \underbrace{(\vec{u}_1, \ldots \vec{u}_k, \ldots, \vec{u}_K)}_{U} \begin{pmatrix} \mu_1 & 0 & 0 & 0 & 0 \\ 0 & \ddots & 0 & 0 & 0 \\ 0 & 0 & \mu_k & 0 & 0 \\ 0 & 0 & 0 & \ddots & 0 \\ 0 & 0 & 0 & 0 & \mu_K \end{pmatrix} (\vec{u}_1, \ldots \vec{u}_k, \ldots, \vec{u}_K)^T = U \mu U^T \quad (32)$$

having the eigenvalues $\mu_i$, $i=1, \ldots$, dim($\underline{c}$) and the associated eigenvectors $\vec{u}_i$. The inversion of the normal matrix separated into its eigenspaces is elementary and reads:

$$N^{-1} = \quad (33)$$

$$\underbrace{(\vec{u}_1, \ldots \vec{u}_k, \ldots, \vec{u}_K)^T}_{U^T} \begin{pmatrix} \frac{1}{\mu_1} & 0 & 0 & 0 & 0 \\ 0 & \ddots & 0 & 0 & 0 \\ 0 & 0 & \frac{1}{\mu_k} & 0 & 0 \\ 0 & 0 & 0 & \ddots & 0 \\ 0 & 0 & 0 & 0 & \frac{1}{\mu_K} \end{pmatrix} (\vec{u}_1, \ldots \vec{u}_k, \ldots, \vec{u}_K)$$

In specific cases, during the inversion in accordance with equation (33), the subspaces of the dim($\underline{c}$)-dimensional target space which are spanned by vectors having very small or even identically vanishing eigenvalues can pose problems since their contributions to the reconstruction can become very large or even infinite. These subspaces correspond to the portions of the tomographic reconstruction which are particularly sensitive to disturbances or are inseparable. Their treatment requires adaptive correction or regulation strategies adapted to the conditions.

In accordance with a further embodiment of the method according to the invention, a deviation of actual manipulator positions of optical individual elements of the optical system from target positions or optimum positions thereof is determined from the measured total aberration distribution.

During the adjustment process, manipulator degrees of freedom $x_\alpha$, $\alpha=1, \ldots, A$ are available with which a suitable cost function F such as, for example, $$F = [G \cdot (\vec{W} - S \cdot \vec{x})]^T \cdot [G \cdot (\vec{W} - S \cdot \vec{x})] + [M \cdot \vec{x}]^T \cdot [M \cdot \vec{x}] \quad (34)$$

is globally minimized. In this case, the measurement values are combined following a defined and unambiguous arrangement to form a column vector $\vec{W}$. A sensitivity matrix S having the elements $S_{k,\alpha}$ is known from design variation calculations and conveys in the liner regime the translation of the manipulator positions into the space of the wavefront deformations at the support points.

A symmetrical measurement value weighting matrix G having the elements $G_{k',k}$ and a matrix of the manipulator weights M having the elements $M_{\alpha,\alpha'}$ serve for regularization. In this case, the matrix elements G and M are selected such that firstly all specification-relevant system characteristic variables are taken into account in a balanced fashion, and secondly the manipulator modulations remain within the predetermined limits.

The minimization of the cost function F leads, finally, to the regularized least squares equation $$\vec{x}_{LSQ} = [(G \cdot S)^T \cdot (G \cdot S) + M \cdot M]^{-1} \cdot (G \cdot S)^{-1} \cdot \vec{W} \quad (35)$$

for the optimum manipulator positions or the target positions of the manipulators.

FIG. 7a shows the optical system according to FIG. 2a in a similar illustration. While the beam path is indicated schematically in FIG. 2a, FIG. 7a shows the optical path of two test beams 774 and 775 between the first optical element 717 and the measurement region 761 in the image plane 711. The test beam 774, illustrated in a dashed fashion, comprises the entire radiation that impinges on one of the first facet elements 719. The test beam 774 is reflected by said facet element onto one of the second facet elements 723, where an image of the source plasma 747 arises. Afterward, the test beam 774 impinges successively on the mirrors 725, 727 and 729 before it illuminates the entire object field 731. For the purposes of measurement, rather than a structure-bearing mask a mirror is arranged at the location of the object field 731, said mirror reflecting the impinging radiation. In contrast to the structure-bearing mask, accordingly, no diffraction takes place at the object field, rather the test beams are reflected into the projection lens 707 without being changed. In the projection lens, the test beam 774 impinges successively on the mirrors 733, 735, 737, 741, 743 and 745 before it impinges on the measurement region 761 in the image plane 711. The test beam 775 basically has a similar path. However, the test beam 775 begins at a different first facet element 719 and is accordingly reflected onto a different second facet element 723. Afterward, the test beam 775 impinges successively on the mirrors 725, 727 and 729, before it likewise illuminates the entire object field 731. In the projection lens, the test beam 775 impinges successively on the mirrors 733, 735, 737, 741, 743 and 745 before it impinges on the measurement region 761 in the image plane 711. FIG. 7a shows that the two test beams 774 and 775 pass through the optical system on different optical paths. While the test beams 774 and 775 are clearly separated at some mirrors (717, 721, 729), they form overlapping impingement regions at other mirrors (725, 727). These different optical paths enable the algorithmic reconstruction of properties of the optical system on the basis of measurement values of the test beams at the location of the measurement region.

Figure 7B:
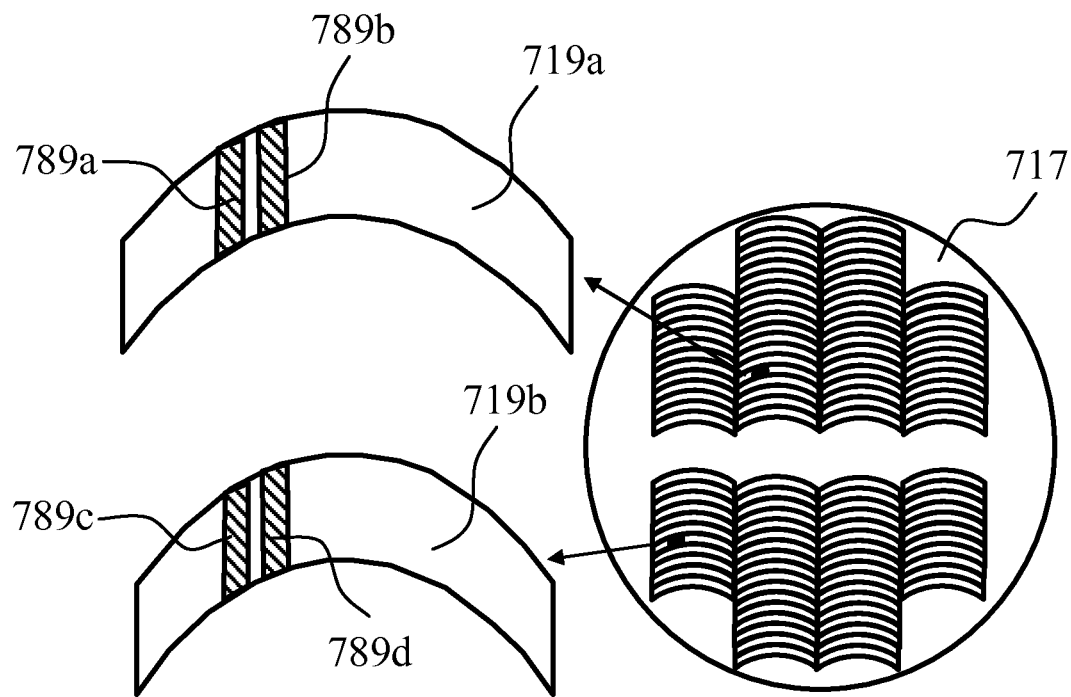
Figure 7C:
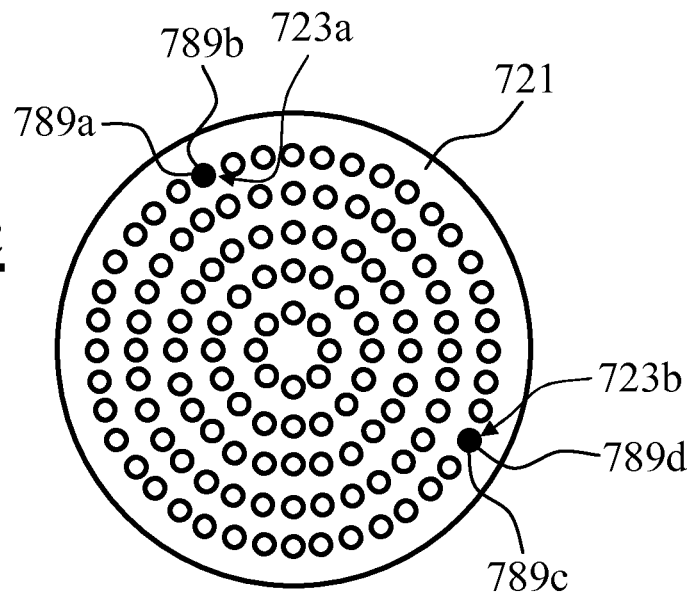
Figure 7G:
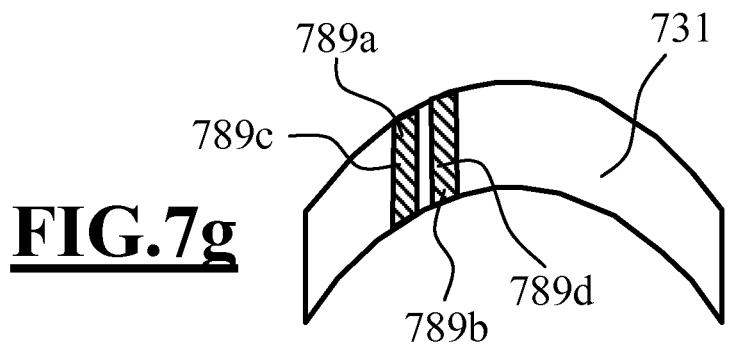
Figure 7H:
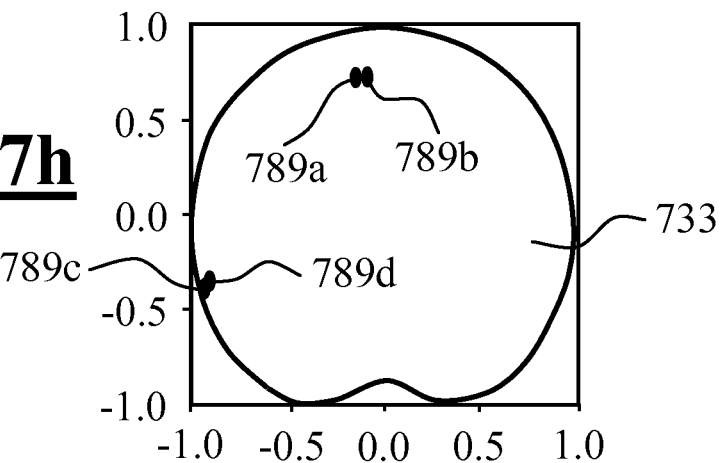
Figure 7I:
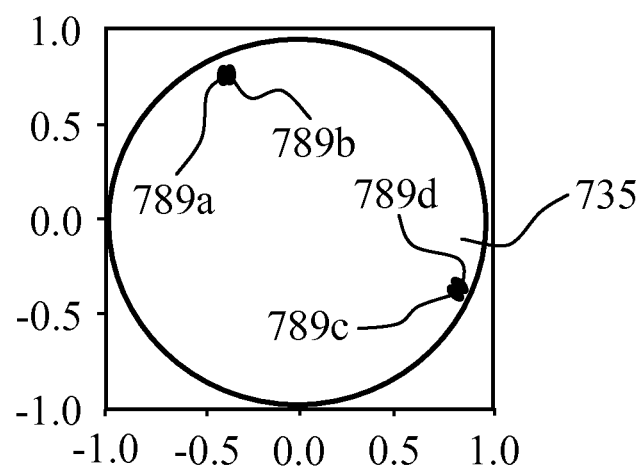
Figure 7J:
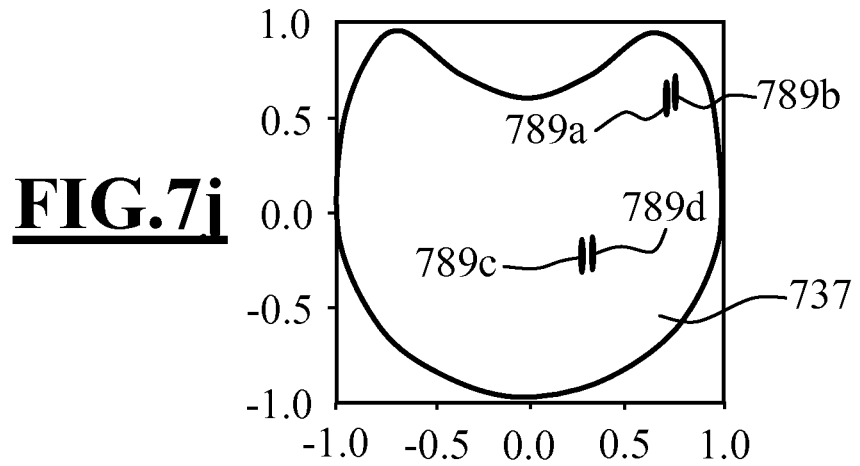
Figure 7K:
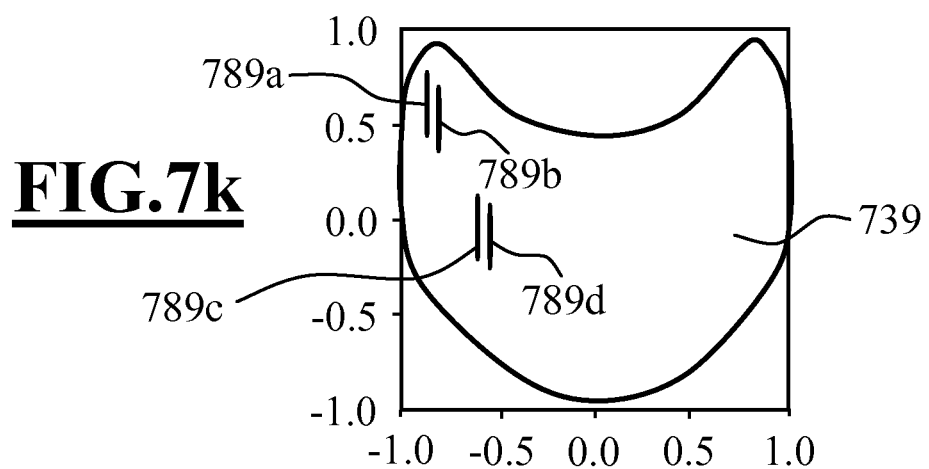
Figure 7L:
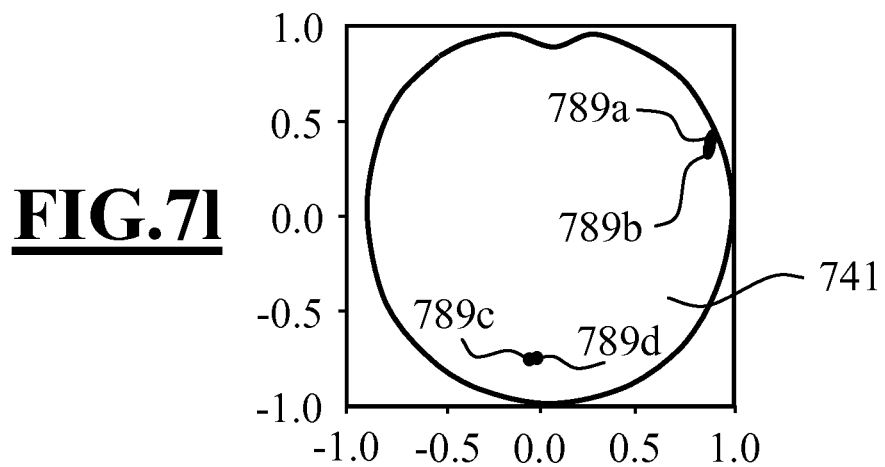
Figure 7M:
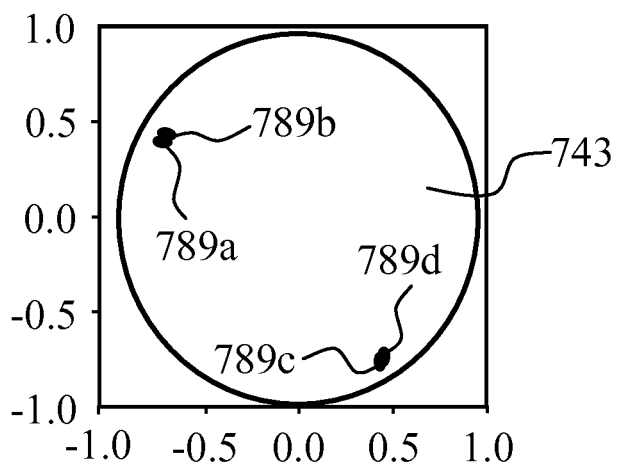
Figure 7N:
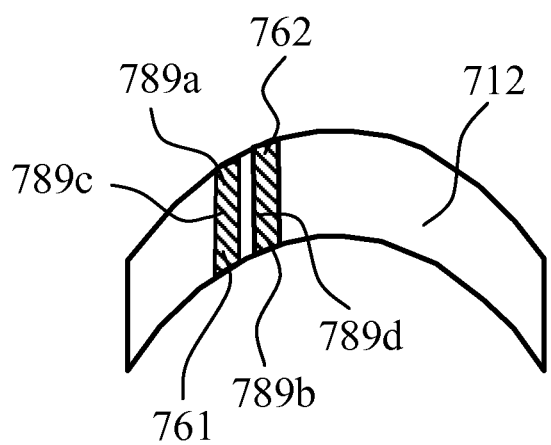
Figure 8A:
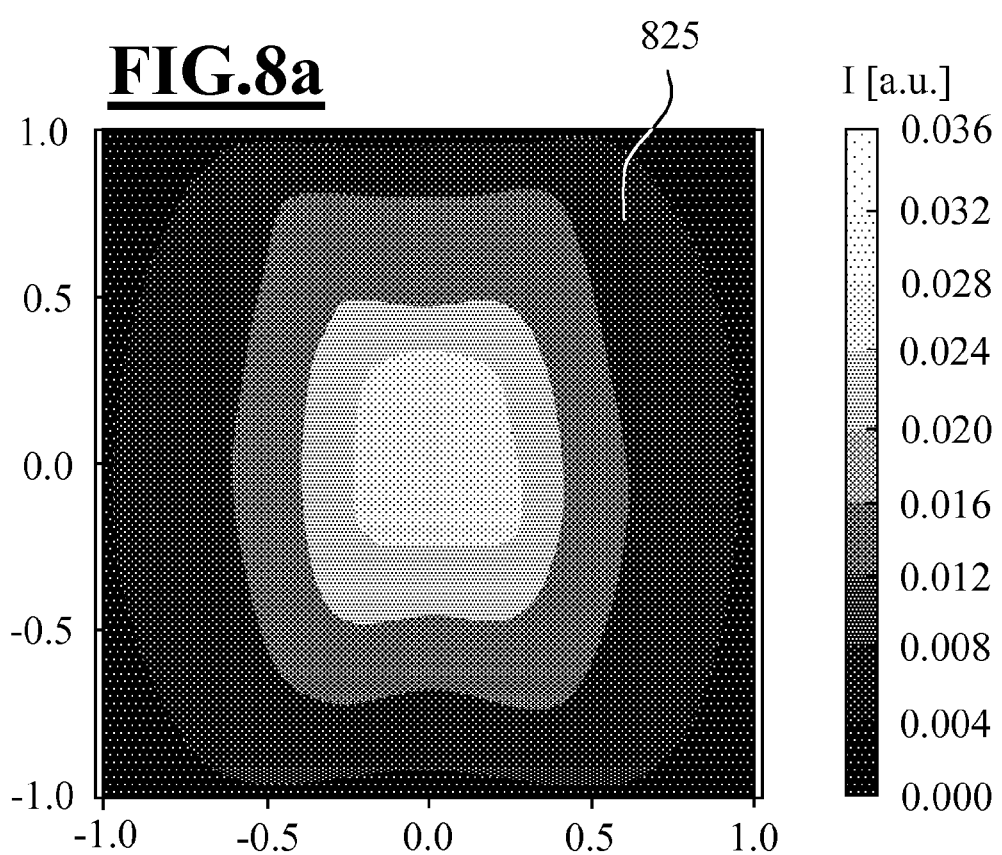
Figure 8B:
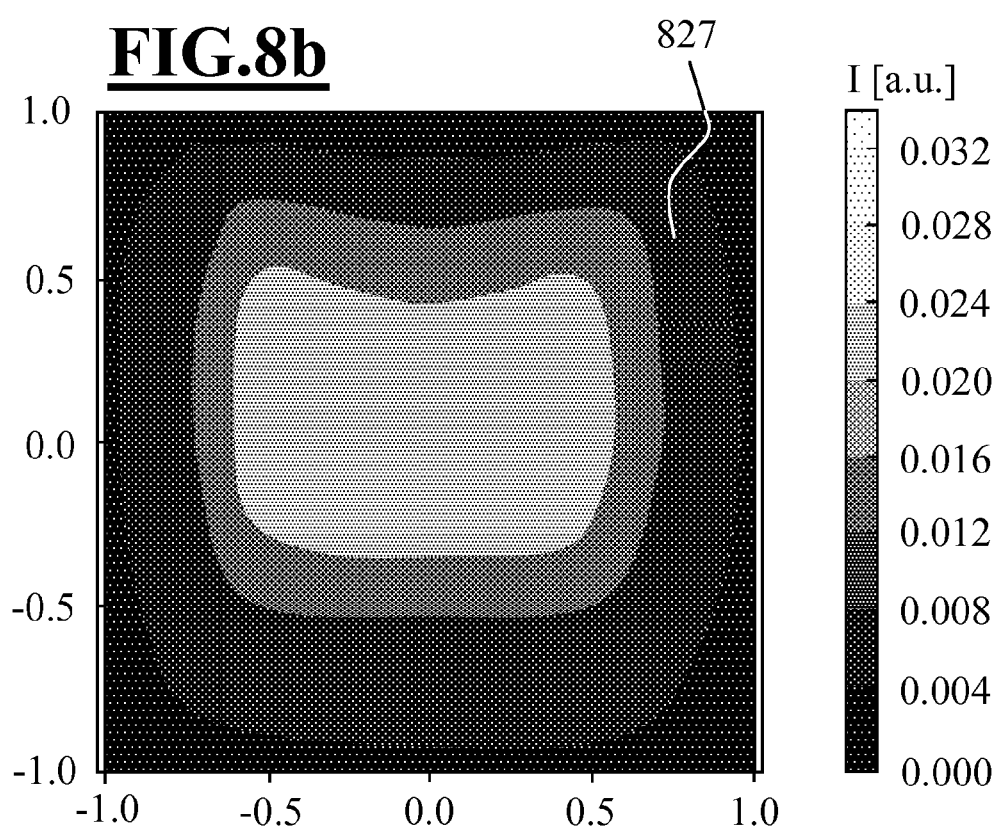
Figure 8E:
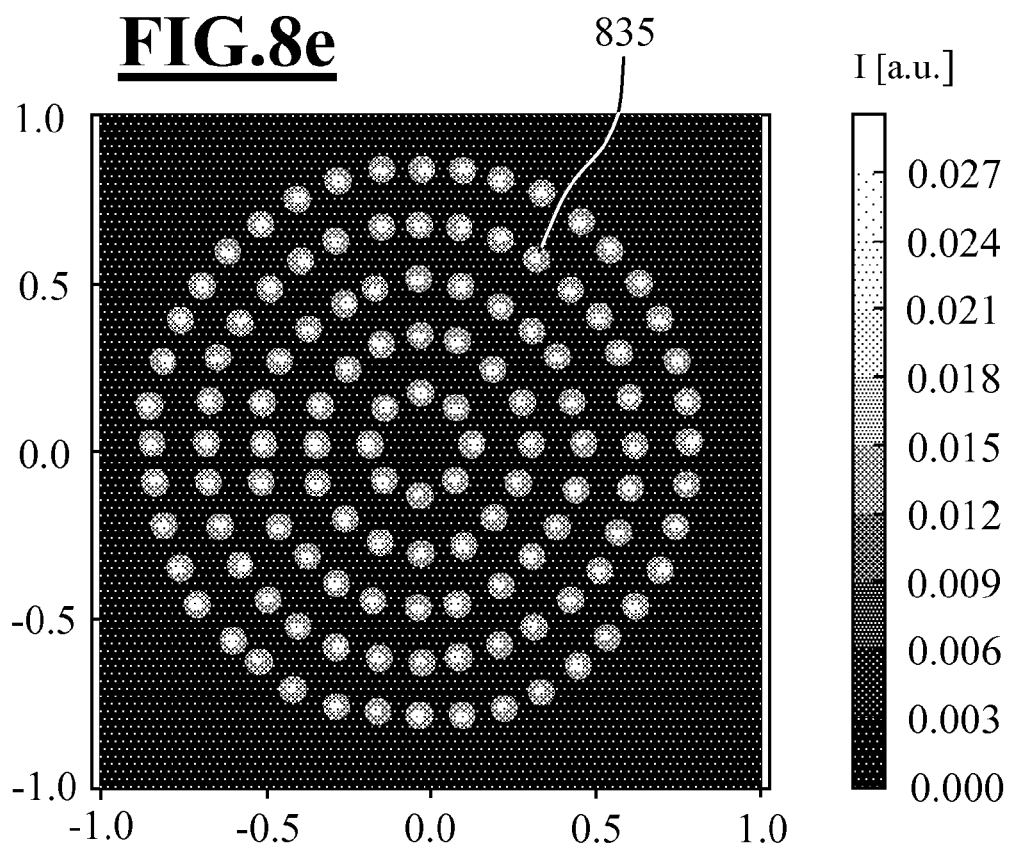
Figure 8F:
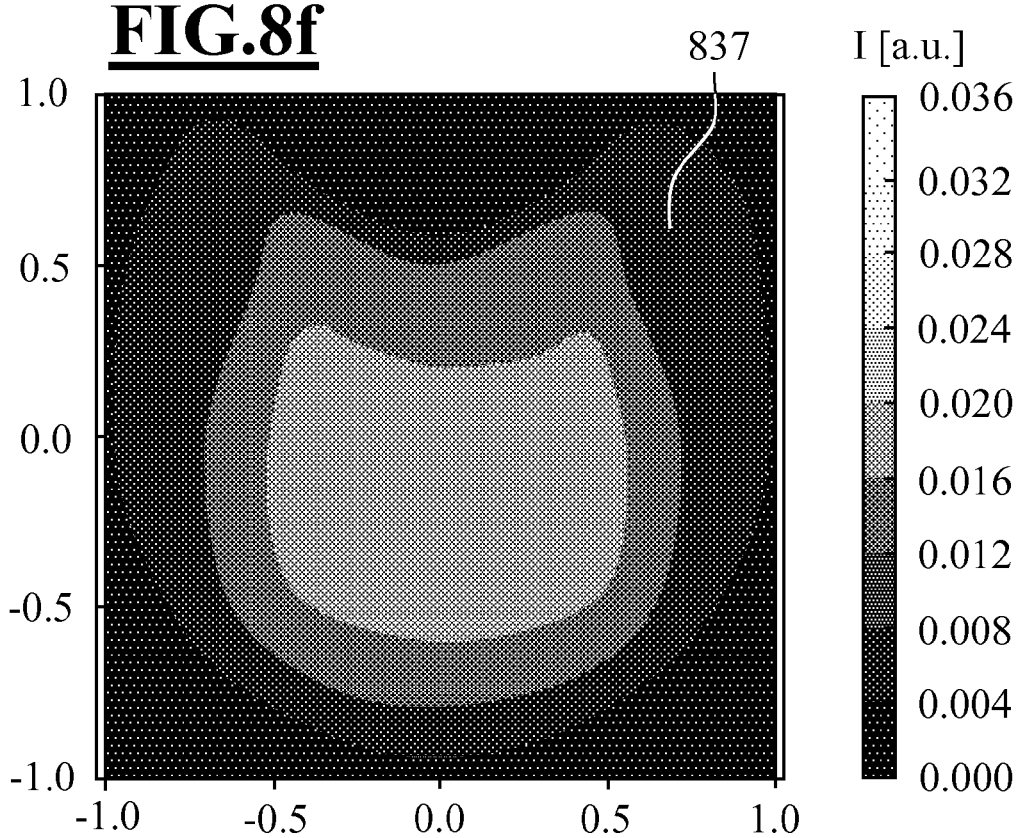
Figure 8G:
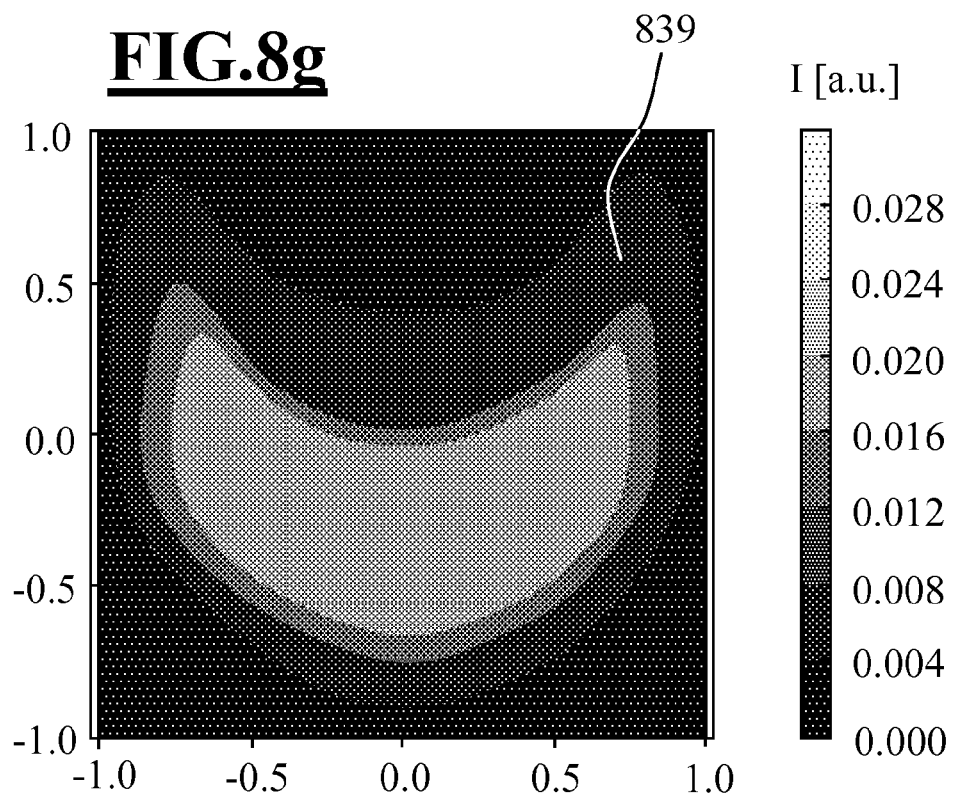
Figure 8H:
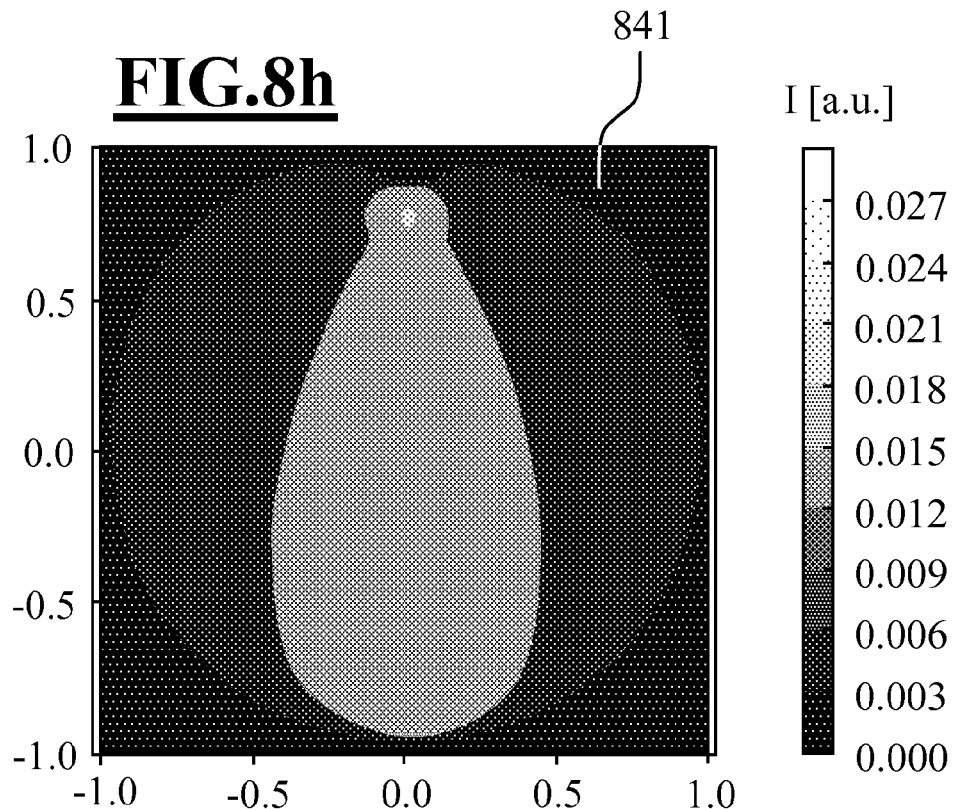
Figure 9G:
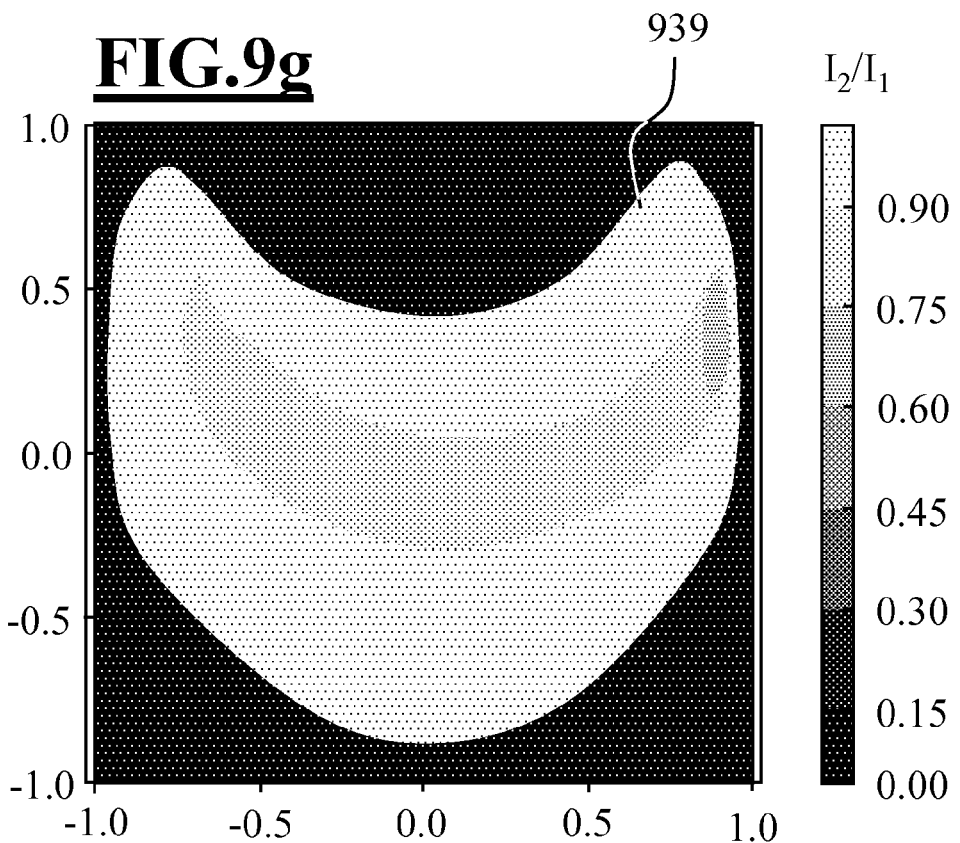
Figure 9H:
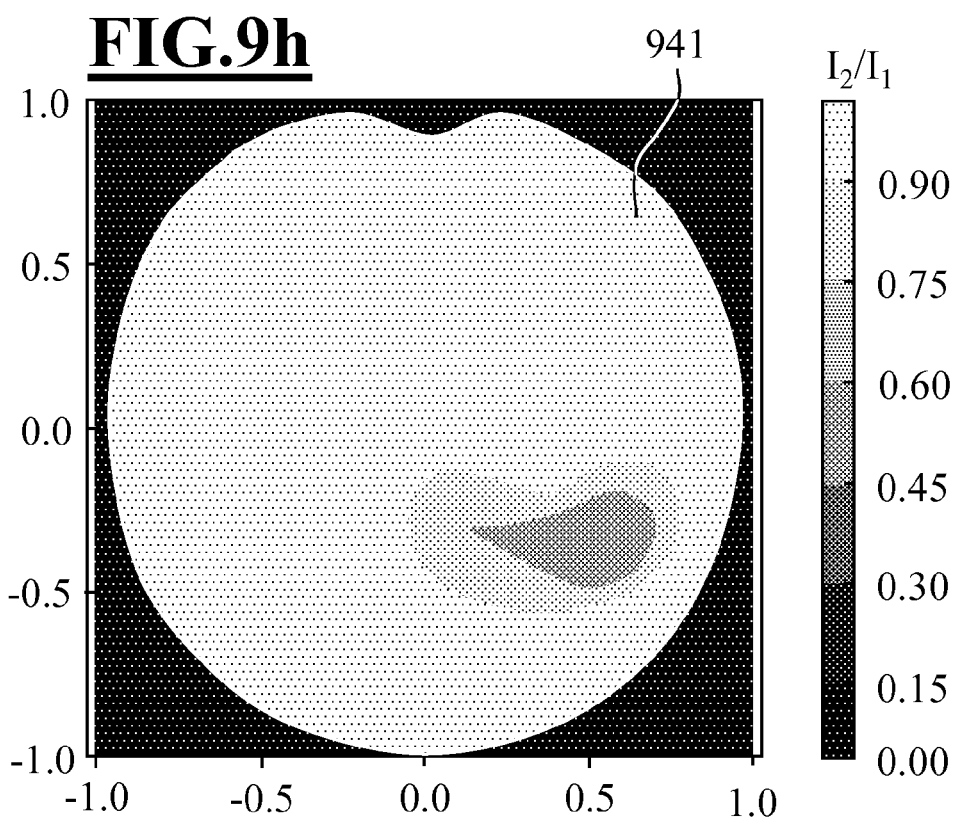

FIGS. 7b to 7n show the impingement regions 789a, 789b, 789c, 789d of four test beams at different locations in the optical system according to FIG. 7a. FIG. 7b shows a plan view of the first optical element 717 and an enlarged illustration of two selected first facet elements 719a and 719b. Four test beams begin at the two selected first facet elements 719a, 719b, said test beams being defined by the impingement regions 789a, 789b, 789c, 789d on the first facet elements 719a and 719b. The first facet element 719a has an orientation such that it directs the impinging radiation onto the second facet element 723a, which is illustrated in FIG. 7c. An image of the source plasma 747 arises at the location of the second facet element 723a. Since both the test beam that proceeds from the impingement region 789a and the test beam that proceeds from the impingement region 789b contribute to the arising of the image, the impingement regions 789a and 789b overlap at the location of the second facet element 723a (FIG. 7c). The impingement regions 789c and 789d correspondingly overlap at the location of the second facet element 723b. FIGS. 7d, 7e and 7f show the impingement regions 789a, 789b, 789c, 789d on the mirrors 725, 727 and 729 respectively. FIG. 7g shows a plan view of the object field 731. Since the second facet elements 723 together with the downstream optics comprising the mirrors 725, 727 and 729 image the first facet elements 719 in a superimposing fashion onto the object field, the form of the object field 731 corresponds to the form of the first facet elements 719. The impingement regions 789a and 789c, and 789b and 789d likewise coincide. The further FIGS. 7h, 7i, 7j, 7k, 7l and 7m show the impingement regions 789a, 789b, 789c, 789d on the mirrors 733, 735, 737, 739, 741 and 743, respectively. FIG. 7n illustrates the image field 712 in the image plane. Since the projection lens images the object field 731 onto the image field 712, FIG. 7n substantially corresponds to FIG. 7g. The impingement regions 789a and 789c form a measurement region 761, and the impingement regions 789b and 789c form a measurement region 762.

FIGS. 8a to 8i illustrate the diagnosis distribution of the radiation intensity on the surfaces of the mirrors 825, 827, 829, 833, 835, 837, 839, 841 and 843. In this case, 13 disjoint measurement regions were defined, and 120 test beams for each measurement region. The number of test beams corresponds to the number of first facet elements and the number of second facet elements as illustrated in FIGS. 2b and 2c. The test beams are chosen such that each test beam is reflected by exactly one facet element of the first facet elements along the optical path. The diagnosis distributions of the radiation intensity on the surfaces of the mirrors 825, 827, 829, 833, 835, 837, 839, 841 and 843 are obtained from the measurement values of the radiation power for these test beams at the location of the respective measurement regions according to the method explained in connection with FIG. 4. For this case, the correction factor was set to be equal to one for all the test beams. Since the diagnosis distribution of the radiation intensity for this reason does not permit a quantitative evaluation anyway, the result values are plotted in "arbitrary units" ([a.u.]).

FIGS. 9a to 9i show the temporal change in the diagnosis distribution on the respective mirrors after a contamination has deposited on the second mirror 935 of the projection lens. The ratio of the diagnosis distribution for the radiation intensity after the deposition to the diagnosis distribution for the radiation intensity in the undisturbed state is illustrated. Each of FIGS. 9a to 9i therefore corresponds to FIGS. 4b and 4c, which have been explained in detail above. With reference to FIGS. 9a to 9i, it is then possible to draw conclusions about the type of disturbance. By way of example, the disturbance is definitely not present on mirror 929, since such a periodic structure of a contamination is not realistic. In the present case, the periodic structure is an artifact resulting on account of the 13 measurement regions. The mirrors 925, 927 and 939 should also be ruled out, since a locally delimited disturbance is expected which is not distributed over a large area over the mirror surface. Therefore, four mirrors have already been able to be ruled out. Clearly, the disturbance cannot be assigned to one mirror in this way. In particular, it is difficult to distinguish between the mirrors 935 and 943 since both are arranged in proximity to a pupil plane and are thus conjugate with respect to one another. Through subsequent correction steps and renewed measurements, the optical system can progressively be brought to an operationally ready state again. Such a correction step involves the cleaning of the mirrors with the aid of atomic hydrogen. Such cleaning methods for eliminating contamination on mirrors for the EUV wavelength range are known from DE102008000551A1, for example. The cleaning can be distinctly accelerated using the measurement of the optical system according to the invention, since it is already possible to determine beforehand which mirrors are presumably damaged.

Figure 10A:
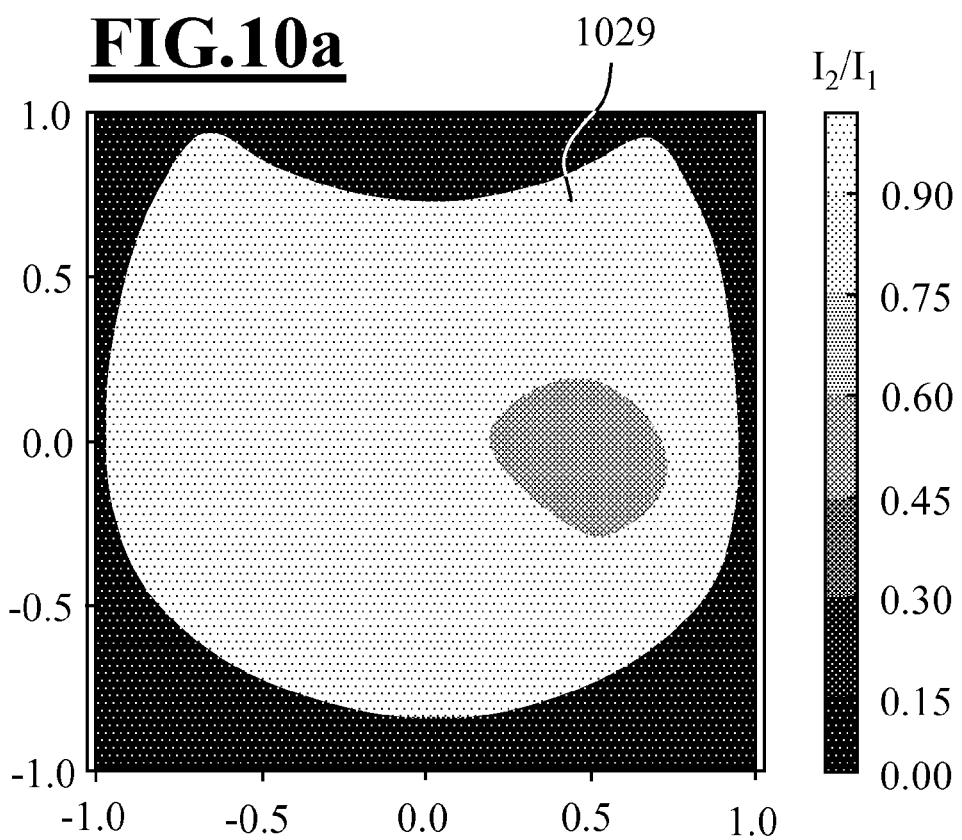
FIGS. 10a and 10b show the damage to two surfaces within the projection lens.
Figure 10B:
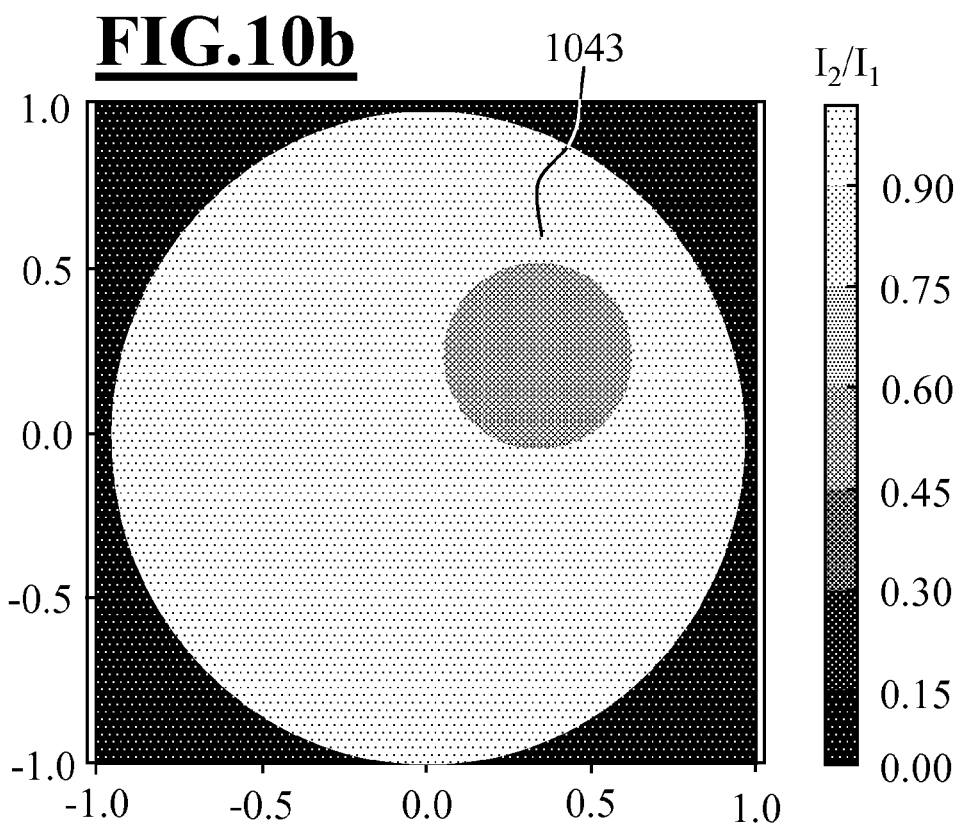
Figure 10C:
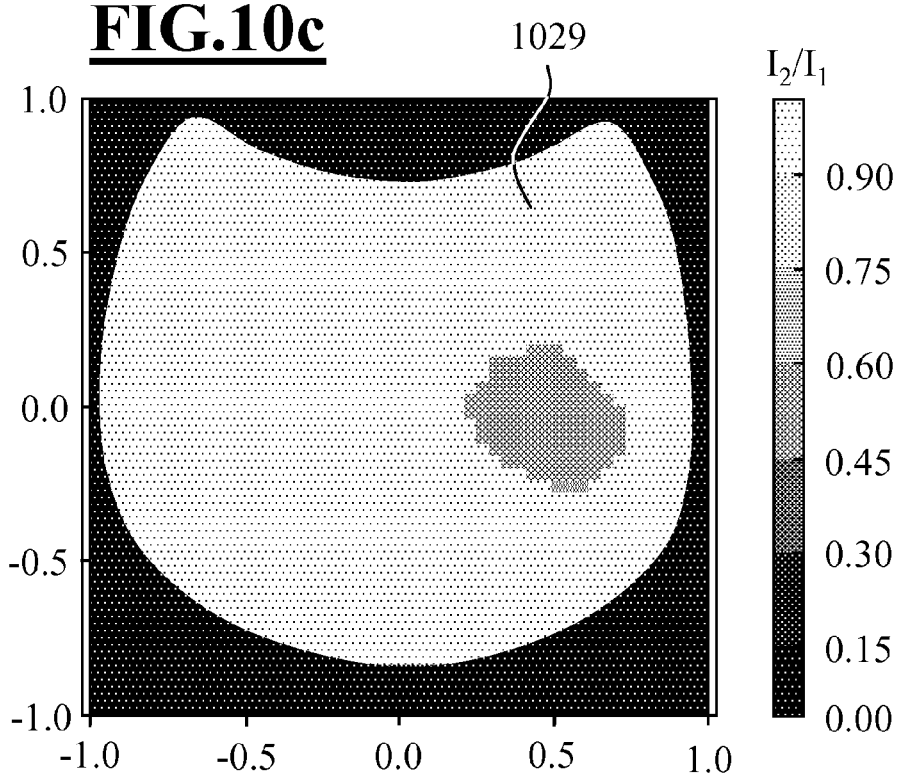
FIGS. 10c and 10d show the result of a reconstruction method for the damage to two surfaces within the projection lens.
Figure 10D:
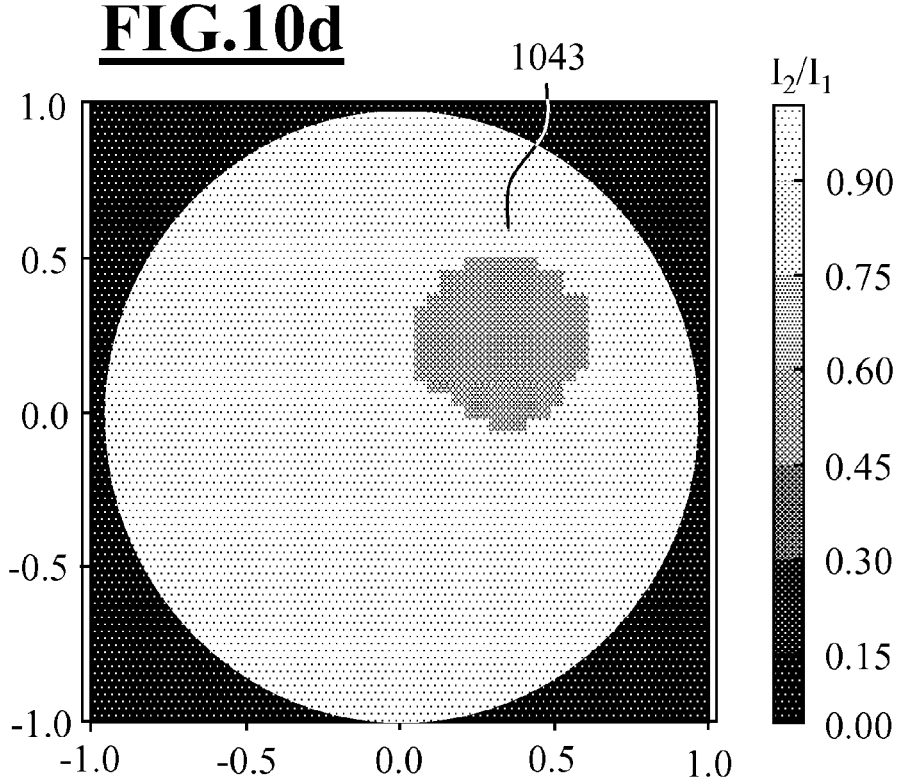

In one developed form of the invention, the calculation method explained in connection with FIG. 4a can be applied in order to unambiguously calculate the contamination of one or a plurality of surfaces. FIG. 10a illustrates damage to the surface 1029, and FIG. 10b illustrates damage to the surface 1043. In both cases, the reflectivity is reduced by half. If the system is then measured with the aid of 13 measurement regions and in each case 120 test beams and if the algorithmic reconstruction method is applied, then FIGS. 10c and 10d are attained as reconstruction. It can clearly be discerned that with the aid of the algorithm it is possible to determine unambiguously that the damage is present on the surfaces 1029 and 1043. Furthermore, a very good reproduction of the form of the respective damage is obtained. A rastered representation of the damage arises on account of the finite number of interpolation points of the function system.

The above description of the preferred embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. A method for measuring an optical system at a measurement plane, comprising:
    passing a first plurality of test beams of radiation through the optical system so as to impinge on exactly one first measurement region in the measurement plane, wherein the test beams of the first plurality of test beams pass through the optical system on optical paths that differ in pairs and impinge on the first measurement region at angles of incidence that differ in pairs with respect to the measurement plane,
    passing a second plurality of test beams of radiation through the optical system so as to impinge on exactly one second measurement region in the measurement plane, wherein the test beams of the second plurality of test beams pass through the optical system on optical paths that differ in pairs and impinge on the second measurement region at angles of incidence that differ in pairs with respect to the measurement plane, wherein the second measurement region differs from the first measurement region, detecting at least one associated measurement value of a first test beam measurement variable at the first measurement region using a first measuring device for each test beam of the first plurality of test beams, detecting at least one associated measurement value of a second test beam measurement variable at the second measurement region using a second measuring device for each test beam of the second plurality of test beams, determining an associated impingement region on at least one reference surface of the optical system using a database for each test beam of the first plurality of test beams and of the second plurality of test beams, wherein the impingement region associated with a test beam is defined as the surface region of the at least one reference surfaceon which radiation of the respective test beam impinges, and calculating a spatial diagnosis distribution of the radiation intensity on the at least one reference surface from the measurement values and the impingement regions for each test beam.

2. The method as claimed in claim 1, wherein the optical system comprises a projection lens which images an object plane onto an image plane, and wherein the measurement plane corresponds to the image plane of the projection lens.

3. The method as claimed in claim 1, wherein the optical system comprises an illumination optical unit for illuminating an object plane, and wherein the measurement plane corresponds to the object plane of the illumination optical unit.

4. The method as claimed in claim 1, wherein the first measurement variable is identical to the second measurement variable.

5. The method as claimed in claim 1, wherein the at least one reference surface corresponds to a surface of an optical element of the optical system.

6. The method as claimed in claim 1, wherein the at least one reference surface is a virtual surface corresponding to no surface of an optical element of the optical system.

7. The method as claimed in claim 1, wherein the entire radiation impinging at the first measurement region is decomposed into the first plurality of test beams in accordance with respective angles of incidence of the first plurality of test beams, and the entire radiation impinging at the second measurement region is decomposed into the second plurality of test beams in accordance with respective angles of incidence of the second plurality of test beams.

8. The method as claimed in claim 7, wherein the measuring device measures the associated radiation power of the radiation of the test beam for each test beam of the first plurality and of the second plurality of test beams.

9. The method as claimed in claim 8, wherein the spatial diagnosis distribution of the radiation intensity on the at least one reference surface is calculated by a procedure in which an average radiation intensity is assigned to each impingement region, wherein the average radiation intensity of an impingement region is defined as the radiation power of the associated test beam at the location of the measurement region on which the test beam impinges, divided by the area content of the impingement region multiplied by a correction factor associated with the test beam, a plurality of points on the reference surface are determined using a database, at least one of the impingement regions is assigned to each point of the plurality of points or an assignment of at least one of the impingement regions to each point is determined using a database, wherein an impingement region is deemed to be assigned to a point exactly when the point lies within the impingement region, a radiation intensity is assigned to each point of the plurality of points on the reference surface, which radiation intensity results from summing the average radiation intensities of the impingement regions which are assigned to the respective point.

10. The method as claimed in claim 9, wherein the correction factor for each test beam is equal to one.

11. The method as claimed in claim 9, wherein the correction factor for each test beam corresponds to the reciprocal of an attenuation experienced by the radiation power of the associated test beam along the optical path between the at least one reference surface and the measurement plane.

12. The method as claimed in claim 9, wherein the correction factors for each test beam are determined using a database.

13. The method as claimed in claim 2, wherein the optical system comprises an illumination optical unit having a plurality of mirrors having optical surfaces for illuminating an object field in the object plane with radiation having a wavelength in the range of 5-15 nm, and the projection lens comprises a plurality of mirrors having optical surfaces and is designed for imaging radiation having a wavelength in the range of 5-15 nm, wherein the illumination optical unit comprises at least one first mirror having a plurality of first facet elements and a second mirror having a plurality of second facet elements, and wherein each test beam of the first plurality of test beams and of the second plurality of test beams is reflected by exactly one first facet element and by exactly one second facet element along the optical path.

14. A non-transient computer-readable medium for operating a measuring system for an optical system, comprising:

computer program instructions for processing items of information about a first plurality of test beams of radiation which pass through the optical system so as to impinge on exactly one first measurement region in a measurement plane, wherein the test beams of the first plurality of test beams pass through the optical system on optical paths that differ in pairs and impinge on the first measurement region at angles of incidence that differ in pairs with respect to the measurement plane, computer program instructions for processing items of information about a second plurality of test beams of radiation which pass through the optical system so as to impinge on exactly one second measurement region in the measurement plane, wherein the test beams of the second plurality of test beams pass through the optical system on optical paths that differ in pairs and impinge on the second measurement region at angles of incidence that differ in pairs with respect to the measurement plane, wherein the second measurement region differs from the first measurement region, computer program instructions for determining associated impingement regions on at least one reference surface of the optical system, wherein the associated impingement region for each test beam of the first plurality of test beams and of the second plurality of test beams on at least one reference surface of the optical system is determined using a database, and wherein the impingement region associated with a test beam is defined as the surface region of the at least one reference surface on which radiation of the respective test beam impinges, computer program instructions for reading in measurement values of a first measurement variable of the radiation impinging at the first measurement region, computer program instructions for reading in measurement values of a second measurement variable of the radiation impinging at the second measurement region, computer program instructions for determining and assigning an associated measurement value for each test beam of the first plurality of test beams, computer program instructions for determining and assigning an associated measurement value for each test beam of the second plurality of test beams, and computer program instructions for generating a spatial diagnosis distribution of the radiation intensity on at least one reference surface from the measurement values and the impingement regions for each test beam of the first plurality and of the second plurality of test beams.

15. The computer program product as claimed in claim 14, wherein the optical system comprises a projection lens, which images an object plane onto an image plane, and wherein the measurement plane corresponds to the image plane of the projection lens.

16. The computer program product as claimed in claim 14, wherein the optical system comprises an illumination optical unit for illuminating an object plane, and wherein the measurement plane corresponds to the object plane of the illumination optical unit.

17. The computer program product as claimed in claim 14, wherein the first measurement variable is identical to the second measurement variable.

18. The computer program product as claimed in claim 14, further comprising:
computer program instructions for reading in angles of incidence and measurement values for the measurement variable of the entire radiation impinging at the first measurement region,
computer program instructions for reading in angles of incidence and measurement values for the measurement variable of the entire radiation impinging at the second measurement region,
computer program instructions for defining the first plurality of test beams in accordance with the angles of incidence read in,
computer program instructions for defining the second plurality of test beams in accordance with the angles of incidence read in,
computer program instructions for determining and assigning an associated measurement value for each test beam of the first plurality of test beams, and
computer program instructions for determining and assigning an associated measurement value for each test beam of the second plurality of test beams.

19. The computer program product as claimed in claim 18, wherein the measurement variable is the radiation power of the impinging radiation,
wherein the computer program instructions for determining and assigning an associated first measurement value for each test beam of the first plurality of test beams determine the radiation power within each test beam of the first plurality of test beams and allocate the associated first measurement value to the respective test beam as an associated measurement value, and wherein the computer program instructions for determining and assigning an associated second measurement value for each test beam of the second plurality of test beams determine the radiation power within each test beam of the second plurality of test beams and allocate the associated second measurement value to the respective test beam as an associated measurement value.

20. The computer program product as claimed in claim 19, wherein the computer program instructions for generating the spatial diagnosis distribution of the radiation intensity comprise:
sub-instructions which assign an average radiation intensity to each impingement region, wherein the average radiation intensity of an impingement region is defined as the radiation power of the associated test beam at the measurement region on which the test beam impinges, divided by the area content of the impingement region multiplied by a correction factor associated with the test beam,
sub-instructions for defining a plurality of points on the at least one reference surface or for determining the plurality of points using a database,
sub-instructions which assign one or a plurality of impingement regions to each point of the plurality of points or determine an assignment of one or a plurality of impingement regions to each point using a database, wherein an impingement region is deemed to be assigned to a point exactly when the point lies within the impingement region, and
sub-instructions for assigning a radiation intensity to each point of the plurality of points on the at least one reference surface, which radiation intensity results as the sum of the average radiation intensities of the impingement regions which are assigned to the respective point.

21. The computer program product as claimed in claim 20, wherein the correction factor for each test beam is equal to one.

22. The computer program product as claimed in claim 21, wherein the correction factor for each test beam corresponds to the reciprocal of an attenuation experienced by the radiation power of the associated test beam along the optical path between the at least one reference surface and the measurement plane.

23. The computer program product as claimed in claim 20, comprising computer program instructions for determining the respective correction factors for each test beam in accordance with data stored in a database.

24. The computer program product as claimed in claim 14, further comprising
computer program instructions for storing the spatial diagnosis distribution in a memory,
computer program instructions for loading a further spatial diagnosis distribution from a memory, and
computer program instructions for comparing a first diagnosis distribution with the further diagnosis distribution.

25. The computer program product as claimed in claim 24, wherein the computer program instructions for comparing a first diagnosis distribution with the further diagnosis distribution contain: sub-instructions for forming the ratio between the first and the further diagnosis distributions.

26. A microlithography projection exposure apparatus comprising a computer system comprising the computer program product as claimed in claim 14.

27. A method for monitoring an optical system, comprising:
measuring the optical system in accordance with the method as claimed in claim 1 at a first point in time, resulting in a first spatial diagnosis distribution and at a second point in time, resulting in a second spatial diagnosis distribution, determining a change between the first and the second spatial diagnosis distributions.

28. A method for monitoring an optical system and a light source unit which provides radiation for operating the optical system, comprising:

measuring the optical system in accordance with the method as claimed in claim 1 at a first point in time resulting in a first spatial diagnosis distribution of a reference surface and at a second point in time resulting in a second spatial diagnosis distribution of the reference surface, wherein the measurement of the optical system is carried out using the radiation of the light source unit, determining a change between the first and the second spatial diagnosis distributions, and determining changes in at least one of a spatial and a spectral emission characteristic of the light source unit from the change between the first and the second spatial diagnosis distributions.

29. The method as claimed in claim 27, wherein determining the change between the first and the second spatial diagnosis distributions comprises: forming a ratio between the first and the second diagnosis distributions.

30. A method for correcting an optical system, comprising:

measuring the optical system in accordance with the method as claimed in claim 1, resulting in the spatial diagnosis distribution of a reference surface, carrying out a correction of the optical system in accordance with the spatial diagnosis distribution of the reference surface.

31. The method as claimed in claim 1, wherein the second measurement device differs from the first measurement device.

* * * * *

UNITED STATES PATENT AND TRADEMARK OFFICE
CERTIFICATE OF CORRECTION

| | |
|---|---|
| PATENT NO. | : 8,786,849 B2 |
| APPLICATION NO. | : 13/913212 |
| DATED | : July 22, 2014 |
| INVENTOR(S) | : Thomas Korb et al. |

It is certified that error appears in the above-identified patent and that said Letters Patent is hereby corrected as shown below:

In the Specification:
Column 1; Line 44; change "a such a" to -- such a --.

Column 16; Line 59; change "possible Likewise." to -- possible. Likewise --.

Column 17; Line 49; change "(LPP)" to -- (LPS) --.

Column 28; Line 2; change "above-mentioned" to -- abovementioned --.

Column 29; Line 44; change "$\beta 2 \leq 0$" to -- $\beta 2 \geq 0$ --.

Column 30; Line 4; change "wk" to -- Wk --.

In the Claims:
Column 35; Line 21; in Claim 1 change "surfaceon" to -- surface on --.

Column 36; Line 24; in Claim 13 change "claim 2 ," to -- claim 2, --.

Column 37; Line 23; in Claim 15 change "computer program product" to -- medium --.

Column 37; Line 28; in Claim 16 change "computer program product" to -- medium --.

Column 37; Line 33; in Claim 17 change "computer program product" to -- medium --.

Column 37; Line 36; in Claim 18 change "computer program product" to -- medium --.

Column 37; Line 58; in Claim 19 change "computer program product" to -- medium --.

Signed and Sealed this
Twenty-fifth Day of August, 2015

Michelle K. Lee
*Director of the United States Patent and Trademark Office*

In the Claims:

Column 38; Line 8; in Claim 20 change "computer program product" to -- medium --.

Column 38; Line 35; in Claim 21 change "computer program product" to -- medium --.

Column 38; Line 38; in Claim 22 change "computer program product" to -- medium --.

Column 38; Line 44; in Claim 23 change "computer program product" to -- medium --.

Column 38; Line 48; in Claim 24 change "computer program product" to -- medium --.

Column 38; Line 56; in Claim 25 change "computer program product" to -- medium --.

Column 38; Lines 62-63; in Claim 26 change "computer program product" to -- medium --.